(12) United States Patent
Narita et al.

(10) Patent No.: US 8,962,650 B2
(45) Date of Patent: Feb. 24, 2015

(54) THERAPEUTIC AGENT FOR TUMOR

(75) Inventors: Yusuke Narita, Tsukuba (JP); Junji Matsui, Tsukuba (JP); Yasuhiro Funahashi, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/002,018

(22) PCT Filed: Apr. 16, 2012

(86) PCT No.: PCT/JP2012/060279
§ 371 (c)(1),
(2), (4) Date: Sep. 9, 2013

(87) PCT Pub. No.: WO2012/144463
PCT Pub. Date: Oct. 26, 2012

(65) Prior Publication Data
US 2014/0031384 A1    Jan. 30, 2014

(30) Foreign Application Priority Data
Apr. 18, 2011 (JP) ................... 2011-091969

(51) Int. Cl.
| A61K 31/437 | (2006.01) |
| A61K 31/4353 | (2006.01) |
| A61K 31/47 | (2006.01) |
| C07D 215/48 | (2006.01) |

(52) U.S. Cl.
CPC ............. *A61K 31/47* (2013.01); *A61K 31/437* (2013.01); *C07D 215/48* (2013.01)
USPC ...................................................... 514/300

(58) Field of Classification Search
CPC ................. A61K 31/437; A61K 31/4353
USPC .................................................. 514/300
See application file for complete search history.

(56) References Cited

U.S. PATENT DOCUMENTS

| | | |
|---|---|---|
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |

(Continued)

FOREIGN PATENT DOCUMENTS

| CA | 2 361 057 | 7/2000 |
| CH | 656535 | 7/1986 |

(Continued)

OTHER PUBLICATIONS

Amendment filed in JP App. Ser. No. No. 2008-532141, filed Jul. 5, 2013, 2 pages (with English translation).
Amendments filed in EP App. Ser. No. 12774278.1, filed Aug. 13, 2013, 12 pages.
Amendment filed on Aug. 6 2013, for JP App. Ser. No. 2009-551518, 6 pages (with English translation).
Amendment in Mexican App. Ser. No. MX/a/2012/014776, dated Oct. 21, 2013, 5 pages.
Submission Document Before the Patent Office re RCE in U.S. Appl. No. 13/205,328, dated Sep. 10, 2013, 12 pages.
Amendment and RCE submission documents filed in U.S. Appl. No. 12/039,381, dated Oct. 23, 2013, 13 pages.

(Continued)

*Primary Examiner* — Niloofar Rahmani
(74) *Attorney, Agent, or Firm* — Fish & Richardson P.C.

(57) ABSTRACT

A therapeutic agent for tumor for combined use of a compound or pharmaceutically acceptable salt thereof represented by Formula (I) and a compound represented by Formula (II):

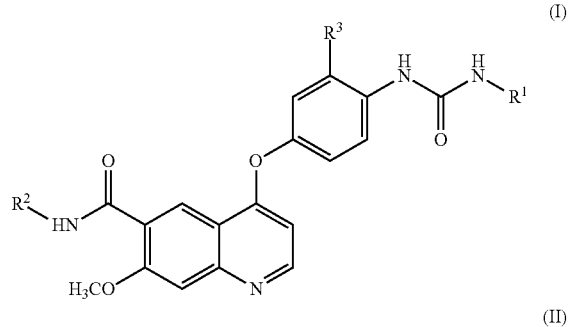

wherein $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom, exhibits an excellent antitumor effect compared to cases where these are individually used.

10 Claims, 2 Drawing Sheets

(56) References Cited

U.S. PATENT DOCUMENTS

| | | |
|---|---|---|
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,242,002 B1 | 6/2001 | Tritthart et al. |
| 6,261,776 B1 | 7/2001 | Pirrung et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |
| 6,596,311 B1 | 7/2003 | Dobetti et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,074,880 B2 | 7/2006 | Rhine et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,211,587 B2 | 5/2007 | Kubo et al |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,725,303 B2 | 5/2010 | Tramontana |
| 7,759,518 B2 | 7/2010 | Maderna et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,994,159 B2 | 8/2011 | Yamamoto et al. |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,470,818 B2 | 6/2013 | Ibrahim et al. |
| 8,492,560 B2 | 7/2013 | Stokes et al. |
| 8,580,254 B2 | 11/2013 | Adam et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2007/0298111 A1 | 12/2007 | Ueki |
| 2008/0207617 A1 | 8/2008 | Miwa et al. |
| 2008/0214604 A1 | 9/2008 | Furitsu et al. |
| 2008/0241835 A1 | 10/2008 | Mehraban et al. |
| 2008/0286282 A1 | 11/2008 | Semba et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0202541 A1 | 8/2009 | Bruns et al. |
| 2009/0209580 A1 | 8/2009 | Matsui |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0020410 A1 | 1/2011 | Nonomura et al. |
| 2011/0060049 A1 | 3/2011 | Vernier et al. |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0207756 A1 | 8/2011 | Matsui |
| 2011/0293615 A1 | 12/2011 | Yamamoto |
| 2012/0022076 A1 | 1/2012 | Maderna et al. |
| 2012/0053177 A1 | 3/2012 | Ibrahim et al. |
| 2012/0077842 A1 | 3/2012 | Bando |
| 2012/0207753 A1* | 8/2012 | Yu et al. .................... 424/134.1 |
| 2012/0219522 A1* | 8/2012 | Xi .................. 424/85.4 |
| 2012/0244217 A1* | 9/2012 | Roth et al. .................... 424/450 |
| 2012/0263677 A1* | 10/2012 | Eagle et al. .................. 424/85.2 |
| 2012/0283206 A1 | 11/2012 | Bruns et al. |
| 2013/0085152 A1 | 4/2013 | Matsui et al. |
| 2013/0123274 A1 | 5/2013 | Nakagawa et al. |
| 2013/0296365 A1 | 11/2013 | Bando |

FOREIGN PATENT DOCUMENTS

| | | |
|---|---|---|
| CN | 1293041 | 5/2001 |
| CN | 1473041 | 2/2004 |
| CN | 1478078 | 2/2004 |
| CN | 1634043 | 7/2005 |
| CN | 1772052 | 5/2006 |
| CN | 1890220 | 1/2007 |
| CN | 101001629 | 7/2007 |
| CN | 101029022 | 9/2007 |
| CN | 101198590 | 6/2008 |

(56) References Cited

FOREIGN PATENT DOCUMENTS

| | | |
|---|---|---|
| CN | 101316590 | 12/2008 |
| CN | 101454311 | 6/2009 |
| CN | 101616671 | 12/2009 |
| CN | 102470133 | 5/2012 |
| EP | 0 203 126 | 12/1986 |
| EP | 0 297 580 | 1/1989 |
| EP | 0 405 425 | 1/1991 |
| EP | 0 408 496 | 1/1991 |
| EP | 0 427 519 | 5/1991 |
| EP | 0 602 851 | 6/1994 |
| EP | 0 684 637 | 11/1995 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 860 433 | 8/1998 |
| EP | 0 870 842 | 10/1998 |
| EP | 0 930 305 | 7/1999 |
| EP | 0 930 310 | 7/1999 |
| EP | 1 029 853 | 8/2000 |
| EP | 1 044 969 | 10/2000 |
| EP | 0 543 942 | 1/2001 |
| EP | 1 153 920 | 11/2001 |
| EP | 1 382 604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 116 246 | 11/2009 |
| EP | 2 119 707 | 11/2009 |
| EP | 2 133 094 | 12/2009 |
| EP | 2 133 095 | 12/2009 |
| EP | 1 415 987 | 5/2010 |
| EP | 2 218 712 | 8/2010 |
| GB | 2253848 | 9/1992 |
| IL | 148756 | 10/2007 |
| IN | 236500 | 11/2009 |
| JP | 61-148115 | 7/1986 |
| JP | 63-028427 | 6/1988 |
| JP | S63-028427 | 6/1988 |
| JP | 1-022874 | 1/1989 |
| JP | 2-291295 | 12/1990 |
| JP | 4-341454 | 11/1992 |
| JP | 6-153952 | 6/1994 |
| JP | 6-287148 | 10/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 10-114655 | 5/1998 |
| JP | 10-147524 | 6/1998 |
| JP | 3088018 | 6/1998 |
| JP | 10-316576 | 12/1998 |
| JP | 11-501343 | 2/1999 |
| JP | H11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-047890 | 2/2001 |
| JP | 2001-131071 | 5/2001 |
| JP | 2002-003365 | 1/2002 |
| JP | 2002-505269 | 2/2002 |
| JP | 2002-114710 | 4/2002 |
| JP | 2002-509872 | 4/2002 |
| JP | 2002-536056 | 10/2002 |
| JP | 2002-536414 | 10/2002 |
| JP | 2003-012668 | 1/2003 |
| JP | 2003-026576 | 1/2003 |
| JP | 2003-252737 | 9/2003 |
| JP | 2003-525595 | 9/2003 |
| JP | 2004-513964 | 5/2004 |
| JP | 2004-155773 | 6/2004 |
| JP | 2004-517859 | 6/2004 |
| JP | 2004-531549 | 10/2004 |
| JP | 2005-272474 | 10/2004 |
| JP | 2005-501074 | 1/2005 |
| JP | 2005-504111 | 2/2005 |
| JP | 2005-124034 | 5/2005 |
| JP | 2005-520834 | 7/2005 |
| JP | 3712393 | 11/2005 |
| JP | 2006-508981 | 3/2006 |
| JP | 2006-515884 | 6/2006 |
| JP | 2006-230816 | 9/2006 |
| JP | 2008-546797 | 12/2008 |
| JP | 2010-535233 | 11/2010 |
| KR | 10-0589032 | 11/2005 |
| WO | WO 86/03222 | 6/1986 |
| WO | WO 92/20642 | 11/1992 |
| WO | WO 93/11748 | 6/1993 |
| WO | WO 94/09010 | 4/1994 |
| WO | WO 95/15758 | 6/1995 |
| WO | WO 95/17181 | 6/1995 |
| WO | WO 95/19774 | 7/1995 |
| WO | WO 96/09294 | 3/1996 |
| WO | WO 96/26997 | 9/1996 |
| WO | WO 96/30347 | 10/1996 |
| WO | WO 96/33980 | 10/1996 |
| WO | WO 96/39145 | 12/1996 |
| WO | WO 96/40080 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | WO 97/17329 | 5/1997 |
| WO | WO 97/21437 | 6/1997 |
| WO | WO 97/38984 | 10/1997 |
| WO | WO 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | WO 98/13350 | 4/1998 |
| WO | WO 98/14437 | 4/1998 |
| WO | WO 98/23613 | 6/1998 |
| WO | WO 98/29137 | 7/1998 |
| WO | WO 98/32436 | 7/1998 |
| WO | WO 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/35146 | 7/1999 |
| WO | WO 99/43654 | 9/1999 |
| WO | WO 99/62890 | 12/1999 |
| WO | WO 00/19985 | 4/2000 |

(56) References Cited

FOREIGN PATENT DOCUMENTS

| | | |
|---|---|---|
| WO | WO 00/31048 | 6/2000 |
| WO | WO 00/42012 | 7/2000 |
| WO | WO 00/43366 | 7/2000 |
| WO | WO 00/43384 | 7/2000 |
| WO | WO 00/44728 | 8/2000 |
| WO | WO 00/47212 | 8/2000 |
| WO | WO 00/50405 | 8/2000 |
| WO | WO 00/71097 | 11/2000 |
| WO | WO 01/02369 | 1/2001 |
| WO | WO 01/23375 | 4/2001 |
| WO | WO 01/27081 | 4/2001 |
| WO | WO 01/32926 | 5/2001 |
| WO | WO 01/36403 | 5/2001 |
| WO | WO 01/40217 | 6/2001 |
| WO | WO 01/45689 | 6/2001 |
| WO | WO 01/47890 | 7/2001 |
| WO | WO 01/47931 | 7/2001 |
| WO | WO 01/60814 | 8/2001 |
| WO | WO 02/16348 | 2/2002 |
| WO | 02/32872 | 4/2002 |
| WO | WO 02/32872 | 4/2002 |
| WO | WO 02/36117 | 5/2002 |
| WO | WO 02/41882 | 5/2002 |
| WO | WO 02/44156 | 6/2002 |
| WO | WO 02/072578 | 9/2002 |
| WO | WO 02/080975 | 10/2002 |
| WO | WO 02/088110 | 11/2002 |
| WO | WO 02/092091 | 11/2002 |
| WO | WO 03/006462 | 1/2003 |
| WO | WO 03/013529 | 2/2003 |
| WO | WO 03/024386 | 3/2003 |
| WO | WO 03/027102 | 3/2003 |
| WO | WO 03/028711 | 4/2003 |
| WO | WO 03/033472 | 4/2003 |
| WO | WO 03/050090 | 6/2003 |
| WO | WO 03/074045 | 9/2003 |
| WO | WO 03/079020 | 9/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/045523 | 6/2004 |
| WO | WO 2004/064730 | 8/2004 |
| WO | 2004/080462 | 9/2004 |
| WO | WO 2004/078144 | 9/2004 |
| WO | WO 2004/080462 | 9/2004 |
| WO | WO 2004/080966 | 9/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/082854 | 9/2005 |
| WO | WO 2005/092896 | 10/2005 |
| WO | WO 2005/117887 | 12/2005 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/038552 | 4/2006 |
| WO | WO 2006/062984 | 6/2006 |
| WO | WO 2006/090930 | 8/2006 |
| WO | WO 2006/090931 | 8/2006 |
| WO | WO 2006/137474 | 12/2006 |
| WO | 2007/002325 | 1/2007 |
| WO | WO 2007/000347 | 1/2007 |
| WO | 2007/015569 | 2/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | 2007/052849 | 5/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | 2007/136103 | 11/2007 |
| WO | WO 2007/136103 | 11/2007 |
| WO | WO 2008/023698 | 2/2008 |
| WO | WO 2008/026748 | 3/2008 |
| WO | 2008/026748 | 6/2008 |
| WO | 2008/088088 | 7/2008 |
| WO | WO 2008/093855 | 8/2008 |
| WO | 2009/060945 | 5/2009 |
| WO | WO 2009/077874 | 6/2009 |
| WO | 2009/096377 | 8/2009 |
| WO | 2009/140549 | 11/2009 |
| WO | WO 2009/140549 | 11/2009 |
| WO | 2010/006225 | 1/2010 |
| WO | 2011/017583 | 2/2011 |
| WO | 2011/022335 | 2/2011 |
| WO | 2011/162343 | 12/2011 |

OTHER PUBLICATIONS

Amendment and Response filed in U.S. Appl. No. 11/997,543, dated Dec. 19, 2013, 38 pages.
Amendment filed in BR App. Ser. No. BR112012032462-4, dated Nov. 4, 2013, 21 pages (with English translation).
Amendment filed in EP App. Ser. No. 12793322.4, dated Nov. 28, 2013, 6 pages.
Amendment filed in KR App. Ser. No. 10-2008-7029472, dated Nov. 20, 2013, 81 pages (with English translation).
Amendment filed in KR App. Ser. No. 10-2013-7020616, dated Nov. 22, 2013, 22 pages (with English translation).
International Preliminary Report on Patentability in International App. Ser. No. PCT/JP2012/060279, dated Oct. 23, 2013, 11 pages.
International Preliminary Report on Patentability in International App. Ser. No. PCT/JP2012/062509, dated Nov. 28, 2013, 11 pages.
Notice of Allowance in IL App. Ser. No. 200090, dated Nov. 18, 2013, 5 pages (with English translation).
Notice of Allowance in JP App. Ser. No. P2009-551518, dated Oct. 22, 2013, 5 pages (with English translation).
Notice of Allowance in KR App. Ser. No. 10-2008-7013685, dated Nov. 29, 2013, 3 pages (with English translation).
Notice of Allowance in U.S. Appl. No. 12/439,339, dated Nov. 7, 2013, 64 pages.
Notice of Allowance in U.S. Appl. No. 12/524,754, dated Nov. 22, 2013, 12 pages.
Office Action in CA App. Ser. No. 2652442, dated Oct. 4, 2013, 2 pages.
Office Action in CN App. Ser. No. 200680020317.5, dated Nov. 28, 2013, 8 pages (with English translation).
Office Action in CN App. Ser. No. 201180030568.2, dated Oct. 12, 2013, 11 pages (with English translation.
Office Action in CO App. Ser. No. 12-022608, dated Dec. 17, 2013, 12 pages (with English translation).
Office Action in IL App. Ser. No. 205512, dated Oct. 28, 2013, 5 pages (with English translation).
Office Action in IL App. Ser. No. 207089, dated Nov. 25, 2013, 6 pages (with English translation).
Office Action in IN App. Ser. No. 1571/CHENP/2007, dated Oct. 23, 2013, 2 pages.
Office Action in IN App. Ser. No. 1571/CHENP/2007, Dec. 9, 2013, 2 pages.
Office Action in MX App. Ser. No. MX/a/2010/008187, dated Dec. 5, 2013, 8 pages (with English translation).
Office Action in MX App. Ser. No. MX/a/2012/002011, dated Nov. 21, 2013, 8 pages (with English translation).
Office Action in U.S. Appl. No. 13/238,085, dated Nov. 12, 2013, 74 pages.

(56) References Cited

OTHER PUBLICATIONS

Office Action in VN App. Ser. No. 1-2011-03484, dated Dec. 31, 2013, 2 pages (with English translation).
Preliminary Amendment filed in EP App. Ser. No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Response filed in CA App. Ser. No. 2652442, dated Jan. 8, 2014, 5 pages.
Response filed in CO App. Ser. No. 12-022608, dated Nov. 13, 2013, 13 pages (with English translation).
Response filed in KR App. Ser. No. 10-2009-7005657, dated Nov. 21, 2013, 46 pages (with English translation).
Response filed in MX App. Ser. No. MX/a/2010/008187, dated Nov. 4, 2013, 21 pages (with English translation).
Response filed in PH App. Ser. No. 1-2011-502441, dated Nov. 4, 2013, 28 pages.
Submission documents re RCE filed in U.S. Appl. No. 11/997,719, dated Dec. 11, 2013, 10 pages.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Voluntary Amendment filed in CA App. Ser. No. 2802644, dated Nov. 22, 2013, 25 pages.
Wang, "Drugs of Today, Everolimus in renal cell carcinoma," Journals on the Web, Aug. 2010, vol. 46, issue 8, 1 page (abstract only).
Berdel el al., "Recombinant Human Stem Cell Factor Stimulates Growth of a Human Glioblastoma Cell Line Expressing c-kit Protooncogenel ", Cancer Research, vol. 52, 1992, p. 3498-3502.
Koyama, N. et al., "Anti-tumor effect of E7080, a novel angiogenesis inhibitor", Folia Pharmacologica Japonica; Nippon Yakurigaku Zasshi, 2008, vol. 132(2):100-104 (with English translation).
Lasota el al., "Mutations in Exons 9 and 13 of KIT Gene Are Rare Events in Gastrointestinal Stromal Tumors", Elsevier, American Journal of Pathology, vol. 157(4), 2000, p. 1091-1095.
Lennartsson et al., "The stem cell factor receptor/c-kit as a drug target in cancer", Current Cancer Drug Targets, vol. 6, 2006, p. 65-75.
Matsui, J. et al., "Mechanism of antitumor activity of E7080, a selective VEGFR and FGFR tyrosine kinase inhibitor (TKI), in combination with selective mutant BRAF inhibition", Journal of Clinical Oncology, May 20, 2010, vol. 29(15), Suppl., ASCO Meeting Abstracts, Part 1, Abstract No: 8567, Jun. 9, 2011.
Turner et al, "Fibroblast growth factor signalling: from development to cancer", Nature Reviews Cancer, vol. 10, 2010, p. 116-129.
Wells et al, "Targeting the RET Pathway in Thyroid Cancer", Clinical Cancer Research, vol. 15, 2009, p. 7119-7123.
Yang, H, et al., "RG7204 (PLX4032), a Selective BRAF V600E Inhibitor, Displays Potent Antitumor Activity in Preclinical Melanoma Models", Cancer Research, Vol. 70(13) , abstract, 2010, p. 5518-5527.
International Search Report for PCT/JP2012/060279, May 29, 2012.
Amendment, Response to Office Action under 37 C.F.R. § 1.111 and Information Disclosure Statement for U.S. Appl. No. 13/624,278, filed Jun. 28, 2013, 23 pages.
Explanation of Circumstances Concerning Accelerated Examination filed May 10, 2012 for JP Patent Application No. 2011-527665, 21 pages (with English Translation).
Japanese Office Action for App. Ser. No. P2008-516724, issued on Oct. 9, 2012 (with English translation).
Matsui et al., "E7080, a novel inhibitor that targets multiple kinases, has potent antitumor activities against stem cell factor producing human small cell lung cancer H146, based on angionenesis inhibition," Int. J. Cancer, 122:664-671 (2008).

Matsui, "Extracellular matrix of linitis plastica as a possible new therapeutic target," Surgical Treatment, Sep. 2003, 89(3):301-306 (with English translation).
Notice of Allowance dated Aug. 7, 2012 for Japanese App. Ser. No. P2007-529565 (with English translation).
Notice of Allowance dated Jul. 17, 2012 for JP App. Ser. No. P2011-527665 (with English translation).
Notice of Allowance dated Sep. 4, 2012 in JP App. Ser. No. P2009-123432 (with English translation).
Notice of Allowance issued in EP App. Ser. No. 10015141.4, dated Jul. 1, 2013, 41 pages.
Office Action dated Nov. 13, 2012 for JP App. Ser. No. P2008-532141 (with English translation).
Request for Substantive Examination for UA App. Ser. No. a201203132, filed Apr. 15, 2013, 14 pages (with English translation).
Response filed in IL App. Ser. No. 195282, filed Jul. 11, 2013, 13 pages (with English translation).
Response to Office Action under 37 C.F.R.S. 1.111 and Information Disclosure Statement for U.S. Appl. No. 11/997,719, filed Jul. 3, 2013, 26 pages.
Amendment filed in KR App. Ser. No. 10-2008-7029472, dated May 1, 2014, 14 pages (with English translation).
Amendment filed in KR App. Ser. No. 10-2009-7005657, dated May 7, 2014, 15 pages (with English translation).
International Preliminary Report on Patentability in PCT App. Ser. No. PCT/US2012/040183, dated Apr. 3, 2014, 9 pages.
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Notice of Allowance in CA App. Ser. No. 2652442, dated Apr. 16, 2014, 1 page.
Notice of Allowance in UA App. Ser. No. a201203132, dated Mar. 21, 2014, 6 pages.
Notice of Allowance in U.S. Appl. No. 12/439,339, dated Apr. 1, 2014, 17 pages.
Notice of Allowance in U.S. Appl. No. 13/205,328, dated May 8, 2014, 10 pages.
Notice of Allowance in VN App. Ser. No. 1-2011-03484, dated Apr. 28, 2014, 2 pages.
Office Action in CN App. Ser. No. 201180030568.2, dated Mar. 24, 2014, 8 pages (with English translation).
Office Action in JP App. Ser. No. P2009-540099, dated Mar. 25, 2014, 6 pages (with English translation).
Office Action in KR App. Ser. No. 10-2008-7029472, dated Mar. 28, 2014, 6 pages (with English translation).
Office Action in KR App. Ser. No. 10-2009-7005657, dated Mar. 28, 2014, 6 pages (with English translation).
Office Action in U.S. Appl. No. 13/805,826, dated Apr. 2, 2014, 8 pages.
Office Action in U.S. Appl. No. 13/923,858, dated Apr. 18, 2014, 64 pages.
Response filed in VN App. Ser. No. 1-2011-03484, dated Feb. 28, 2014, 40 pages (with English translation).
Response to Office Action in EP App. Ser. No. 08704376.6, dated Apr. 30, 2014, 73 pages.
Response to Office Action in U.S. Appl. No. 12/039,381, dated Apr. 3, 2014, 7 pages.
Shumaker et al., "Effect of lenvatinib (E7080) on the QTc interval: results from a thorough QT study in healthy volunteers," Cancer Chemother Pharmacol., published online Mar. 23, 2014, 9 pages.
Submission documents re RCE in U.S. Appl. No. 13/205,328, dated Apr. 28, 2014, 1 page.
Amended claims in EP App. Ser. No. 04807580.8, dated Jun. 16, 2014, 7 pages.
Besson et al., "PTEN/MMAC1/TEP1 in signal transduction and tumorigenesis," EP J Biochem., 1999, 263:605-611.
Dankort et al., "Braf V660E cooperates with Pten loss to induce metastic melanoma," Nature Genetics, 2009, 41(5):544-552.
Davies et al., "Mutations of the BRAF gene in human cancer," Nature, Jun. 27, 2002, 417:949-954.
Finn et al., "A multicenter, open-label, phase 3 trial to compare the efficacy and safety of lenvatinib (E7080) versus sorafenib in first-line

(56) References Cited

OTHER PUBLICATIONS treatment of subjects with unresectable hepatocellular carcinoma," Am Soc Clin Oncol Annual Meeting Abstract TPS4153, May 31, 2014, 5 pages.

Fujii et al., "Angiogenesis Inhibitor/Kekkan Shinsei Sogaiyaku," Clin Gastroenterol., May 25, 2004, 19:220-227 (with English translation).

Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.

Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.

Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210-215.

Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.

Notice of Allowance in U.S. Appl. No. 11/997,719, dated Jun. 5, 2014, 14 pages.

Notice of Allowance in U.S. Appl. No. 12/741,682, dated May 15, 2014, 13 pages.

Notice of Allowance in U.S. Appl. No. 13/624,278, dated Jun. 25, 2014, 57 pages.

Office Action in EP App. Ser. No. 03791389.4, dated Jun. 10, 2014, 4 pages.

Office Action in EP App. Ser. No. 08846814.5, dated Jun. 4, 2014, 4 pages.

Office Action in MX App. Ser. No. MX/a/2010/008187, dated Apr. 28, 2014, 4 pages (with English translation).

Office Action in MX App. Ser. No. MX/a/2012/002011, dated Apr. 28, 2014, 10 pages (with English translation).

Office Action in MX App. Ser. No. MX/a/2012/014776, dated Apr. 4, 2014, 22 pages (with English Translation).

Office Action in RU App. Ser. No. 2012103471, dated May 20, 2014, 5 pages (with English translation).

Office Action in U.S. Appl. No. 11/662,425, dated Jun. 5, 2014, 30 pages.

Office Action in U.S. Appl. No. 12/039,381, dated May 29, 2014, 78 pages.

Office Action in U.S. Appl. No. 13/805,826, dated Jul. 1, 2014, 88 pages.

Official Notification in EP App. Ser. No. 04807580.8, dated Jun. 16, 2014, 1 pages.

Official Notification in EP App. Ser. No. 04807580.8, dated Jun. 27, 2014, 17 pages.

Response to Office Action filed in EP App. Ser. No. 04807580.8, dated May 16, 2014, 13 pages.

Response to Office Action in CA App. Ser. No. 2676796, dated Jun. 27, 2014, 18 pages.

Response to Office Action in CN App. Ser. No. 201180030568.2 filed on May 14, 2014, 10 pages (with English translation).

Response to Office Action in JP App. Ser. No. P2009-540099, dated Apr. 28, 2014, 9 pages (with English Translation).

Response to Office Action in MX App. Ser. No. MX/a/2010/008187, dated Jun. 25, 2014, 5 pages (with English translation).

Response to Office Action in SG App. Ser. No. 201108602-2, dated May 22, 2014, 37 pages.

Response to Office Action in U.S. Appl. No. 11/662,425, filed on May 20, 2014, 8 pages.

Response to Restriction Response in U.S. Appl. No. 13/805,826, dated Jun. 2, 2014, 2 pages.

Schlumberger et al., "A phase 3, multicenter, double-blind, placebo-controlled trial of lenvatinib (E7080) in patients with $^{131}$I-refractory differentiated thyroid cancer (SELECT)," Am Soc Clin Oncol., Annual Meeting Abstract LBA6008, 2014, 4 pages.

Submission Documents re RCE filed in U.S. Appl. No. 12/524,754, dated May 13, 2014, 1 page.

Submission Documents re RCE filed in U.S. Appl. No. 12/741,682, dated May 6, 2014, 1 page.

Submission Documents re RCE filed in U.S. Appl. No. 13/083,338, dated May 6, 2014, 1 page.

Submission in EP App. Ser. No. 04807580.8, dated Jun. 13, 2014, 18 pages.

Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.

Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.

Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 38(6):1059-1066 (with English translation).

Yokota, "ASCO report: Gastrointestinal Cancer field/ASCO Hokoku Shokakigan Ryoiki," Gan Bunshi Hyoteki Chiryo, 2010, 8(4):271-283.

"Carboxymethyl Cellulose Sodium." Chemical Land 21. Retrieved Apr. 24, 2012. http://www.chemicalland21.comlindustrialchem/perfonnancepolymer/CARBOXYMETHYL%20CELLULOSE%20S0DIUM%20SAL_T.htm, 2 pages.

"Carboxymethylcellulose Sodium." Merck Index: An Encyclopedia of Chemicals, Drugs, & Biologicals: 13th Ed. New Jersey: Merck & Co (2001), p. 308.

"Current Protocols in Molecular Biology", John Wiley & Sons Section 11.4-11.13 (1987), 62, pages.

"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.

"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.

"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p. 1-p. 5, XP007919509 (English translation).

"Chapter 2.2 Loslichkeit, Losungsgeschwindigkeit, Loslichkeitsverbesserung," Rudolf Voigt Ed—Voigt R et al., Pharmazeutische Technologie fuer Studium und Beruf, DT. Apotheker-Verl, Stuttgart; DE, Jan. 1, 2000, p. 40-p. 52, XP008143620 (English translation).

"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).

Abrams et al., SU11248 Inhibits KIT and Platelet-derived Growth Factor Receptor Beta in Preclinical Models of Human Small Cell Lung CancerMolecular Cancer Therapeutics., 2: 471-478, 2003.

Abuzar et al., "Synthesis of some new 7-chloro-4-substituted quinolines as potential antiparasitic agents," Eur. J. Med. Chem., 21(1):5-8 (1986).

Agarwal et al., "Binding of discoidin domain receptor 2 to collagen I: an atomic force microscopy investigation," Biochemistry, 41(37):11091-11098 (2002).

Altschul et al., "Basic Local Alignment Search Tool", J. Mol. Biol. 215:403-410 (1990).

Amended Claims filed in EP App. Ser. No. 11798224.9, filed Aug. 2, 2013, 35 pages.

Amended Claims filed in KR App. Ser. No. 10-2010-7011023, filed Jul. 17, 2013, 15 pages (with English translation).

Amended Claims filed in RU App. Ser. No. 2013140169, dated Aug. 29, 2013, 17 pages (with English translation).

(56) References Cited

OTHER PUBLICATIONS

Amended description filed after receipt of search report for EP Patent App. No. 10809938.3, filed Dec. 8, 2011, 2 pages.
Amended description filed after receipt of search report for EP Patent App. No. 10809938.3, filed Sep. 14, 2010, 2 pages.
Amended Specification filed in AU App. Ser. No. 2012246490, filed Aug. 2, 2013, 15 pages.
Amendment after Allowance filed on Jan. 4, 2011 for CA App. Ser. No. 2426461, 12 pages.
Amendment and Argument filed on Apr. 27, 2012 in response to the JP Office Action for JP2007-542863, 13 pages and English translation.
Amendment and Response for Application No. IL Patent Application No. 195282 dated Jul. 11, 2013, 13 pages (with English translation).
Amendment and Response to Final Office Action under 37 C.F.R. §1.116 for U.S. Appl. No. 12/092,539, filed Jun. 15, 2011, 9 pages.
Amendment and Response to Final Office Action under 37 C.F.R. §1.116 for U.S. Appl. No. 12/864,817, filed Dec. 5, 2011, 10 pages.
Amendment and Response to Non-Final Office Action for U.S. Appl. No. 11/997,543, filed Aug. 19, 2011, 34 pages.
Amendment and Response to Office Action under 37 C.F.R § 1.111 for U.S. Appl. No. 12/439,339, dated Aug. 22, 2013, 14 pages.
Amendment and Response to Office Action under 37 C.F.R. § 1.111 dated Apr. 2, 2013 for U.S. Appl. No. 13/083,338, 9 pages.
Amendment and Response to Office Action under 37 C.F.R. §1.111 for U.S. Appl. No. 11/997,719, filed Dec. 23, 2010, 21 pages.
Amendment and Response to Office Action under 37 C.F.R. §1.111 for U.S. Appl. No. 12/092,539, filed Mar. 11, 2011, 9 pages.
Amendment and Response to Office Action under 37 C.F.R. §1.111 for U.S. Appl. No. 12/439,339, filed Feb. 7, 2012, 11 pages.
Amendment and Response to Office Action under 37 C.F.R. §1.111 for U.S. Appl. No. 12/524,754, filed Feb. 17, 2012, 13 pages.
Amendment and Response to Office Action under 37 C.F.R. §1.111 for U.S. Appl. No. 12/7416,82, filed Jul. 30, 2012, 49 pages.
Amendment and Response to Office Action under 37 C.F.R. §1.111 for U.S. Appl. No. 12/864,817, filed Aug. 9, 2011, 12 pages.
Amendment and Response to Office Action under 37 C.F.R. §1.111 for U.S. Appl. No. 13/205,328, filed Apr. 11, 2012, 12 pages.
Amendment and Response to Office Action under 37 C.F.R. §1.116 for U.S. Appl. No. 11/997,543, filed Jan. 9, 2012, 27 pages.
Amendment and Response to Office Action under 37 C.F.R. §1.116 for U.S. Appl. No. 12/439,339, filed Jul. 30, 2012, 9 pages.
Amendment filed in EP App. Ser. No. 12774278.1, filed Aug. 13, 2013, 12 pages.
Amendment filed in JP App. Ser. No. 2008-532141, filed Jul. 5, 2013, 2 pages (with English translation).
Amendment filed in U.S. Appl. No. 13/805,826, dated Sep. 9, 2013, 14 pages.
Amendment filed on Apr. 11, 2006 for CN App. Ser. No. 01819710.8, 35 pages (with English translation).
Amendment filed on Apr. 17, 2002 for TW App. Ser. No. 90125928, 26 pages. (with English translation).
Amendment filed on Apr. 19, 2005 for JP App. Ser. No. 2002-536056, 26 pages (with English translation).
Amendment filed on Aug. 13, 2013 in JP App. Ser. No. P2009-540099, 8 pages (with English translation).
Amendment filed on Aug. 17, 2004 for ZA App. Ser. No. 2003/3567, 39 pages.
Amendment filed on Aug. 29, 2013 in CN App. Ser. No. 201280010898.X, 24 pages (with English translation).
Amendment filed on Aug. 4, 2004 for ZA App. Ser. No. 2003/3567, 95 pages.
Amendment filed on Aug. 6, 2013, for JP App. Ser. No. 2009-551518, 6 pages (with English translation).
Amendment filed on Dec. 12, 2011 for JO Patent App. No. 55/2011, 6 pages (with English translation).
Amendment filed on Dec. 15, 2011 for VN App. Ser. No. 1-2011-03484, 5 pages (with English translation).
Amendment filed on Dec. 22, 2011 for ZA App. Ser. No. 2011/08697, 2 pages.
Amendment filed on Feb. 9, 2011 for TW App. Ser. No. 100104281, 2 pages.
Amendment filed on Jan. 11, 2010 for CN App. Ser. No. 200580026468.7, 4 pages (with English translation).
Amendment filed on Jan. 26, 2010 for CN App. Ser. No. 200710007097.9, 9 pages (with English translation).
Amendment filed on Jul. 2, 2009 for CN App. Ser. No. 200710007097.9, 9 pages (with English translation).
Amendment filed on Jun. 22, 2010 for CN App. Ser. No. 200710007097.9, 9 pages (with English translation).
Amendment filed on Mar. 20, 2012 for KR Patent App. No. 10-2012-7003846, 7 pages.
Amendment filed on Mar. 23, 2009 for JP Patent Application No. 2005-124034, 29 pages (with English translation).
Amendment filed on Mar. 6, 2006 for KR App. Ser. No. 10-2003-7005506, 34 pages (with English translation).
Amendment filed on Mar. 7, 2005 for JP App. Ser. No. 2002-536056, 23 pages (with English translation).
Amendment filed on Mar. 8, 2006 for KR App. Ser. No. 10-2005-7020292, 33 pages (with English translation).
Amendment filed on May 10, 2012 for JP Patent Application No. 2011-527665, 5 pages.
Amendment filed on May 21, 2009 for JP App. Ser. No. 2005-124034, 14 pages (with English translation).
Amendment filed on May 28, 2003 for CN App. Ser. No. 01819710.8, 8 pages (with English translation).
Amendment filed on Nov. 19, 2009 for CN App. Ser. No. 200710007097.9, 9 pages (with English translation).
Amendment filed on Nov. 24, 2011 for KR App. Ser. No. 10-2007-7001347, 7 pages (with English translation).
Amendment filed on Oct. 1, 2013 in IN App. Ser. No. 10502/CHENP/2012, 10 pages.
Amendment filed on Oct. 25, 2005 for KR App. Ser. No. 10-2003-7005506, 53 pages (with English translation).
Amendment filed on Oct. 28, 2011 for LB Patent App. No. 9292, 2 pages.
Amendment filed on Oct. 9, 2006 for CN App. Ser. No. 01819710.8, 28 pages (with English translation).
Amendment filed on Sep. 13, 2005 for CN App. Ser. No. 01819710.8, 51 pages (with English translation).
Amendment filed on Sep. 23, 2009 for CN App. Ser. No. 200580026468.7, 11 pages (with English translation).
Amendment filed on Sep. 23, 2013 in AU App. Ser. No. 2011270165, 35 pages.
Amendment for Chinese Patent Application No. 201080030508.6 dated Feb. 7, 2013, 17 pages with English translation.
Amendment for IN App. Ser. No. 7026/CHENP/2013, dated Sep. 5, 2013, 8 pages.
Amendment in Canadian App. Ser. No. 2828946, dated Aug. 30, 2013, 14 pages.
Amendment in Israeli App. Ser. No. 200090, dated Oct. 2, 2013, 10 pages (with English translation).
Amendment in Korean App. Ser. No. 10-2012-7033886, dated Sep. 27, 2013, 34 pages (with English translation).
Amendment in Mexican App. Ser. No. MX/a/2012/014776, dated Oct. 21, 2013, 10 pages (with English translation).
Amendment in Russian App. Ser. No. 2012158142, dated Oct. 17, 2013, 48 pages (with English translation).
Amendment, Response to Office Action under 37 C.F.R. §1.111 and Information Disclosure Statement fo U.S. Appl. No. 13/624,278, filed Jun. 28, 2013, 23 pages.
Amendments received before examination for EP App. Ser. No. 01976786.2, dated Sep. 10, 2004, 126 pages.
Amendments to the specification filed on Mar. 26, 2012 for AU Patent Appl. No. 2010285740, 15 pages.
American Association for Cancer Research, "Redefining the Frontiers of Science," 94th Annual Meeting, vol. 44, 2nd Edition, Washington Convention Center, Washington, DC (Jul. 11-14, 2003), 3 pages.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.

(56) References Cited

OTHER PUBLICATIONS

Anderson and Flora, "Preparation of Water-Soluble Compounds Through Salt Formation," Practice of Medicinal Chem., 1996, pp. 739-754.
Anderson et al., "Preparation of Water-soluble Compounds through Salt Formation. The Practice of Medicinal Chemistry," *Technomics*, 347-349 and 355-356 (Sep. 25, 1999).
Anonymous, "Scientific Discussion," EMEA, URL: htttp://www.ema.europa.eu/docs/en_GB/document_library/EPARScientific_Discussion/human/000406/WC500022203.pdf, 1-61 (2004) (XP007918143), 62 pages.
Antibodies: A Laboratory Manual, E. Harlow and D. Lane, ed. Cold Spring Harbor Laboratory (Cold Spring Harbour, NY, 1988), 190 pages.
Applicant Interview Summary Under 37 C.F.R § 1.133(b) for U.S. Appl. No. 12/439,339, dated May 31, 2013, 7 pages.
Applicant Observation for CN App. Ser. No. 200780017371.9, filed May 29, 2013, 6 pages (with English translation).
Approval of request for amendments for EP App. Ser. No. 04025700.8, dated Mar. 13, 2008, 1 page.
Argument and Amendment for JP App. Ser. No. 2008-556208, filed Mar. 21, 2013, 15 pages (with English translation).
Argument and Amendment for CN 200880002425.9 filed on Jul. 18, 2011, 8 pages with English translation.
Argument and Amendment for JP App. Ser. No. 2008-532141, filed Nov. 29, 2012, 12 pages (with English translation).
Argument and Amendment for JP. App. Ser. No. 2008-516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Argument Brief filed on Mar. 6, 2006 for KR App. Ser. No. 10-2003-7005506, 45 pages (with English translation).
Argument Brief filed on Mar. 8, 2006 for KR App. Ser. No. 10-2005-7020292, 42 pages (with English translation).
Argument Brief filed on Nov. 24, 2011 for KR App. Ser. No. 10-2007-7001347, 52 pages (with English translation).
Argument Brief filed on Oct. 25, 2005 for KR App. Ser. No. 10-2003-7005506, 20 pages (with English translation).
Argument filed on Apr. 19, 2005 for JP App. Ser. No. 2002-536056, 6 pages (with English translation).
Argument filed on Aug. 13, 2013 in JP App. Ser. No. 2009-540099, 10 pages (with English translation).
Argument filed on Aug. 6, 2013 for JP Patent Application No. 2009-551518, 18 pages (with English translation).
Argument filed on Mar. 23, 2009 for JP App. Ser. No. 2005-124034, 12 pages (with English translation).
Argument filed on May 21, 2009 for JP App. Ser. No. 2005-124034, 5 pages (with English translation).
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al , "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
*Asu no Shinyaku* ("The New Drugs of Tomorrow"), editing/printing by Technomics, Inc., 81-83 (Dec. 2006) (English translation), 14 pages.
Australian ("""AU""") Office Action issued on Oct. 29, 2009 for corresponding AU Application No. 2006285673, 3 pages.
Australian ("AU") Notice of Allowance dated Nov. 22, 2010 for corresponding AU Application No. 2006285673, 3 pages.
Australian ("AU") Office Action issued on May 19, 2010 for corresponding AU Application No. 2006285673, 2 pages.
Australian ("AU") Office Action issued on May 7, 2009 for corresponding AU Application No. 2006285673, 2 pages.
Australian Office Action directed at Appl. No. 2007252506 issued on Nov. 7, 2011, 5 pages.
Australian Office Action directed at Appl. No. 2007252506 issued on Jan. 13, 2012, 2 pages.
Australian Office Action for App. Ser. No. 2008205847, issued on Apr. 11, 2012, 2 pages.
Australian Office Action for App. Ser. No. 2008211952, issued on Apr. 3, 2012, 2 pages.
Australian Office Action for Application No. 2006309551 issued on Feb. 2, 2012, 2 pages.
Australian Office Action for Application No. AU2006309551 issued on Apr. 28, 2011, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012, 81 pages.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Baker et al., "Blockade of vascular endothelial growth factor receptor and epidermal growth factor receptor signaling for therapy of metastatic human pancreatic cancer," Cancer Res., 62:1996-2003 (2002).
Bankston et al., "A Scaleable synthesis of BAY 43/9006: A Potent Raf Kinase Inhibitor for the Treatment of Cancer", Organic Process Res Dev., 6:777-81 (2002).
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," Organic Process Research & Development, 4(5):427-435 (2000) (XP002228592).
Beebe et al., "Pharmacological Characterization of CP-547,632, a Novel Vascular Endothelial Growth Factor Receptor-2 Tyrosine Kinase Inhibitor for Cancer Therapyl", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a RadioresistantTumorType, 57 Cancer Res. 5309-5319 (Dec. 1, 1997).
Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," *Journal of Pharmaceutical Sciences*, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Boissan et al., "c-Kit and c-kit mutations in mastocytosis and other hematological diseases," J. Leukocyte Biol., 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).

(56) References Cited

OTHER PUBLICATIONS

Bonferoni et al, "Influence of medium on dissolution-erosion behavior of Na carboxymethylcellulose and on viscoelastic properties of gels," International journal of pharmaceutics, 1995, vol. 117, No. 1, pp. 41-48.
Bramhall, S., "The Matrix Metalloproteinases and Their Inhibitors in Pancreatic Cancer", International J. Pancreatol., 21, 1-12, 1997.
Brief communication to applicant for EP App. Ser. No. 01976786.2, dated Sep. 9, 2005, 1 page.
Brueggen et al., "Preclinical profile of ABP309, a potent $2^{nd}$ generation VEGF receptor tyrosine kinase inhibitor belonging to the class of aminonicotinamides," EORTC-NCI-AACR Symp Mol Targets Cancer Ther., 2, (Abstract 172), 2004, 2 pages.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Bussolino et al., "Role of Soluble Mediators in Angiogenesis," Eur. J. Cancer, 32A(14):2401-2412 (1996).
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action issued on Jan. 14, 2010 for corresponding CA Application No. 2,620,594, 3 pages.
Canadian ("CA") Office Action issued on Jan. 6, 2011 for corresponding CA Application No. 2,620,594, 3 pages.
Canadian Office Action for App. Ser. No. 2426461, dated Dec. 6, 2007, 5 pages.
Canadian Office Action for App. Ser. No. 2426461, dated Feb. 10, 2010, 2 pages.
Canadian Office Action for App. Ser. No. 2426461, dated May 8, 2009, 2 pages.
Canadian Office Action for App. Ser. No. 2426461, dated Nov. 20, 2008, 3 pages.
CancerCare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999).
Carlomagno et al., "Point Mutation of the RET Proto-Oncogene in the TT Human Medullary Thyroid Carcinoma cell Line", Biochemical and Biophysical Research Communications, 207,1022-1028 (1995).
Carlomagno et al., "BAY 43/9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carter et al , "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated vol. 5, No.Fear of Proteins", Visual Laboratory Notebook Series, Section 6, Immunostaining, pp. 127-163, Shujunsha, Co., Ltd., 1997 (Japanese).
Chen et al., "FGFR3 as a therapeutic target of the small molecule inhibitor PKC412 in hematopoietic malignancies," *Oncogene*, 24:8259-8267 (2005).
Chesi et al., "Activated fibroblast growth factor receptor 3 is an oncogene that contributes to tumor progression in multiple myeloma," *Blood*, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).

Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Chinese ("CN") Office Action issued on Dec. 4, 2009 for corresponding CN Application No. 200680036592.6, 8 pages with English translation.
Chinese Office Action directed at Appl. No. 200780017371 .9 mailed on Oct. 20, 2010, 13 pages with English translation.
Chinese Office Action for App. Ser. No. 200780017371.9, issued on Mar. 7, 2012, 8 pages with English translation.
Chinese Office Action for App. Ser. No. 200880002425.9, issued on Mar. 7, 2012, 7 pages (with English translation).
Chinese Office Action for App. Ser. No. 200880003336.6, issued on May 24, 2011, 24 pages (with English translation).
Chinese Office Action for App. Ser. No. 200880115011.7, issued on Feb. 20, 2012, 10 pages (with English translation).
Chinese Office Action for App. Ser. No. 201080030508.6, issued on Nov. 30, 2012, 13 pages, (with English translation).
Chinese Office Action for Application No: 200680041355.9 issued on Mar. 5, 2010, 21 pages (with English translation).
Chinese Office Action for Application No: 200680041355.9 issued on Aug. 24, 2010, 10 pages (with English translation).
Chinese Office Action for CN 200680020317.5 dated Aug. 3, 2012 with English translation, 11 pages.
Chinese Office Action with the English translation dated, Feb. 29, 2012, for Application No. 200680036592.6, 7 pages.
Chinese Response to Office Action directed at Appl. No. 200780017371 .9 filed on Feb. 24, 2011, 10 pages with English translation.
Chinese Response to Office Action for Application No: 200680041355.9 filed on Jul. 19, 2010, 4 pages with English translation.
Chinese Response to Office Action for Application No:200680041355.9 filed on Nov. 8, 2010, 6 pages with English translation.
Chinese Response to the Chinese Decision of Rejection, filed on Feb. 7, 2013, for corresponding Chinese Application No. 200680036592.6, 27 pages.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," *Int. J. Cancer*, 98:463-469 (2002).
CIPO Notice of Allowance for Appl. No. 2,620,594 dated May 3, 2012, 1 page.
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors," Clin. Cancer Res., 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
CN200780032071.8 Office Action issued on Oct. 13, 2010, 29 pages with English translation.
CN200780032071.8 Response to Office Action filed on Feb. 16, 2011, 62 pages with English translation.
CN200880003336.6 Response to Office Action filed on Oct. 8, 2011, 10 pages.
Cohen et al., "Expression of Stem Cell Factor and c-kit in Human Neuroblastoma," Blood, 84(10):3465-3472 (1994).
Colombian Office Action for App. Ser. No. 12-022608, dated Oct. 7, 2013, 10 pages (with English translation).
Communication about intention to grant a European patent for EP App. Ser. No. 01976786.2, dated Sep. 4, 2006, 173 pages.

(56) References Cited

OTHER PUBLICATIONS

Communication about intention to grant a European patent for EP App. Ser. No. 04025700.8, dated Oct. 15, 2007, 392 pages.
Communication about intention to grant a European patent for EP App. Ser. No. 06023078.6, dated Jul. 18, 2008, 169 pages.
Communication about intention to grant a European patent for EP App. Ser. No. 05783232.1, dated Nov. 20, 2008, 70 pages.
Communication from the Examining Division for EP App. Ser. No. 01976786.2, dated Aug. 17, 2005, 4 pages.
Communication from the Examining Division for EP App. Ser. No. 01976786.2, dated Mar. 21, 2006, 3 pages.
Communication from the Examining Division for EP App. Ser. No. 01976786.2, dated Sep. 19, 2005, 4 pages.
Communication from the Examining Division for EP App. Ser. No. 04025700.8, dated Oct. 23, 2006, 2 pages.
Communication from the Examining Division for EP App. Ser. No. 05783232.1, dated Feb. 7, 2008, 1 pages.
Communication from the Examining Division for EP App. Ser. No. 06023078.6, dated Aug. 2, 2007, 1 page.
Communication from the Examining Division for EP App. Ser. No. 06023078.6, dated Sep. 26, 2007, 2 pages.
Communication regarding the expiry of opposition period for EP App. Ser. No. 01976786.2, dated Jan. 4, 2008, 1 page.
Communication regarding the expiry of opposition period for EP App. Ser. No. 04025700.8, dated May 7, 2009, 1 page.
Communication regarding the expiry of opposition period for EP App. Ser. No. 05783232.1, dated Feb. 19, 2010, 1 page.
Communication regarding the expiry of opposition period for EP App. Ser. No. 06023078.6, dated Nov. 4, 2009, 1 page.
Continuation Patent Application, Preliminary Amendment and Information Disclosure Statement for U.S. Appl. No. 13/923,858, filed Jun. 21, 2013, 97 pages.
Corbin et al., "Sensitivity of oncogenic KIT mutants to the kinase inhibitors MLN518 and PD180970", Blood., 104, 3754-3757, 2004.
Corvi et al., "RET IPCM-1: a novel fusion gene in papillary thyroid carcinoma", Oncogene, 19: 4236-4242 (2000).
Croom et al., "Imatinib mesylate," Drugs, 63(5):513-522 (2003).
Da Silva et al., "A novel germ-line point mutation in RET exon 8 (Gly(533)Cys) in a large kindred with familial medullary thyroid carcinoma," *J. Clin. Endocrinol. Metab.*, 88:5438-5443 (2003).
David et al., "A Phase I Trial of the Epidermal Growth Factor Receptor (EGFR)—Directed Bispecific Antibody (BsAB) MDX-447 in Patients with Solid Tumors. (Meeting abstract).", ASCO 18: 433, Abstract 1999.
De Lange et al., "Phase II trial of cisplatin and gemcitabine in patients with advanced gastric cancer," Annals of Oncology, 15:484-488 (2004).
Decision of Final Rejection issued in CN App. Ser. No. 200780017371.9, dated Jul. 3, 2013, 16 pages (with English translation).
Decision of Rejection mailed on Oct. 30, 2012 issued for corresponding Chinese Application No. 200680036592.6, 8 pages with full English language translation.
Decision to grant a European patent for EP App. Ser. No. 01976786.2, dated Feb. 1, 2007, 2 pages.
Decision to grant a European patent for EP App. Ser. No. 04025700.8, dated Jun. 5, 2008, 2 pages.
Decision to grant a European patent for EP App. Ser. No. 05783232.1, dated Mar. 19, 2009, 2 pages.
Decision to grant a European patent for EP App. Ser. No. 06023078.6, dated Dec. 4, 2008, 2 pages.
Deficiencies in sequence listing for EP App. Ser. No. 06023078.6, dated Dec. 5, 2006, 3 pages.
Demand for Appeal Trial filed in JP App. Ser. No. 2008-532141, filed Jul. 5, 2013, 10 pages (with English translation).
Deplanque et al., "Anti-Angiogenic Agents: Clinical Trial Design and Therapies in Development," *European Journal of Cancer*, 36:1713-1724 (2000).
Dermer, "Another Anniversary for the War on Cancer," *Bio/Technology*, 12:320 (1994).

Di Lorenzo et al., "Targeted Therapy in the Treatment of Metastatic Renal Cell Cancer", Oncology, 77(Suppl.1):122-131 (2010).
Di Raimondo et al., "Antiogenic Factors in multiple myeloma: higher levels in bone than in peripheral blood," *Haematologica*, 85:800-805 (2000).
Dias et al., "IL-12 Regulates VEGF and MMPs in a Murine Breast Cancer Model", International J. Cancer., 78, 361-5, 1998.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
EP Communication under Rule 71(3) EPC for Application No. 06832529.9 issued on Nov. 25, 2011, 35 pages.
EP07806561.2 Office Action issued on Dec. 9, 2011, 5 pages.
EP07806561.2 Office Action issued on Feb. 7, 2011, 1 page.
EP07806561.2 Response to Office Action filed on Aug. 9, 2011, 134 pages.
Erber et al., "Combined inhibition of VEGF and PDGF signaling enforces tumor vessel regression by interfering with pericyte-mediated endothelial cell survival mechanisms," *FASEB J.*, 18(2):338-340 (2004).
European Office Action for App. Ser. No. 04719054.1, issued on Oct. 30, 2009, 5 pages.
European Office Action for App. Ser. No. 04807580.8, issued on Apr. 18, 2011, 11 pages.
European Office Action for App. Ser. No. 04807580.8, issued on Dec. 3, 2010, 7 pages.
European Office Action for App. Ser. No. 04807580.8, issued on Oct. 25, 2011, 17 pages.
European Office Action for App. Ser. No. 04818213.3, issued on Feb. 2, 2012, 5 pages.
European Office Action for App. Ser. No. 07743994.1, issued on Oct. 10, 2012, 8 pages.
European Office Action for Application No. 06832529.9 issued on Oct. 15, 2009, 1 page.
European Office Action for Application No. 06832529.9 issued on Sep. 12, 2011, 3 pages.
European Response to EESR directed at Appl. No. 07743994.1-2123 filed on Nov. 23, 2010, 22 pages.
European Response to Office Action for Application No. 06832529.9 filed on Apr. 22, 2010, 82 pages.
European Response to Office Action for Application No. 06832529.9 filed on Oct. 4, 2011, 27 pages.
European Search Report dated Jul. 23, 2010 for European application No. 06782407, 8 pages.
European Search Report dated May 4, 2010 for European Application No. 07743994, 9 pages.
European Search Report directed at application No. 06768437.3, issued on Oct. 11, 2010, 10 pages.
European Search Report directed at application No. 06832529.9, issued on Jul. 29, 2009, 6 pages.
European Search Report directed at application No. 06833681.7, issued on Nov. 24, 2010, 15 pages.
European Search Report directed at application No. 07806561.2, issued on Jan. 19, 2011, 16 pages.

(56) References Cited

OTHER PUBLICATIONS

European Search Report directed at application No. 10015141.4, issued on Sep. 9, 2011, 6 pages.
European Search Report for App. Ser. No. 03791389.4, issued on Jul. 7, 2011, 5 pages.
European Search Report for App. Ser. No. 04025700.8, dated Jan. 13, 2005, 3 pages.
European Search Report for App. Ser. No. 04719054.1, issued on Apr. 17, 2009, 4 pages.
European Search Report for App. Ser. No. 04818213.3, issued on Jul. 30, 2007, 3 pages.
European Search Report for App. Ser. No. 05783232.1, issued on Sep. 7, 2007, 5 pages.
European Search Report for App. Ser. No. 06023078.6, issued on Mar. 16, 2007, 5 pages.
European Search Report for App. Ser. No. 06767145.3, issued on May 23, 2011, 7 pages.
European Search Report for App. Ser. No. 10809938.3, issued on Jan. 2, 2013, 5 pages.
European Search Report for EP 08704376.6 dated Jun. 14, 2012, 12 pages.
Examination Report dated Feb. 18, 2005 for NZ App. Ser. No. 525324, 1 page.
Examination Report dated Feb. 21, 2008 for AU App. Ser. No. 2006203099, 2 pages.
Examination Report dated Jan. 30, 2013 for AU App. Ser. No. 2009210098, 10 pages.
Examination Report dated Mar. 26, 2008 for AU App. Ser. No. 2006236039, 2 pages.
Examination Report dated May 4, 2006 for AU App. Ser. No. 2001295986, 2 pages.
Examination Report dated Nov. 24, 2012 for AU App. Ser. No. 2008325608, 3 pages.
Examination Report dated Oct. 13, 2003 for NZ App. Ser. No. 525324, 2 pages.
Examination Report dated Sep. 2, 2004 for NZ App. Ser. No. 525324, 1 page.
Examination Report dated Sep. 20, 2005 for AU App. Ser. No. 2001295986, 3 page.
Examination report from EP 04025700 mailed Apr. 10, 2006, 3 pages.
Experimental Medicine, Supplementary Volume, "A New Handbook of Genetic Engineering", Section 4, Yodosha, 2003(Japanese).
Explanation of Circumstances Concerning Accelerated Examination filed May 10, 2012 for JP Patent Application No. 2011-527665, 18 pages (with English Translation).
Extended European Search Report dated Feb. 21, 2013 for EP App. Ser. No. 12195436.6, 8 pages.
Extended European Search Report for App. Ser. No. 08846814.5, issued on Jun. 18, 2012, 11 pages.
Extended European Search Report mailed on Dec. 7, 2012 issued in connection with Corresponding European Application No. 06797249.7, 6 pages.
Ezzat et al., "Dual Inhibition of RET and FGFR4 Retains Medullary Thyroid Cancer Cell Growth," Clinical Cancer Research, Feb. 2005, 11:1336-1341.
Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
First Office Action issued on Mar. 6, 2012 for the corresponding JP application, JP2007-542863, 17 pages and English translation.
Folkman et al., "Angiogenesis," *The Journal of Biological Chemistry*, 267(16):10931-10934 (1992).
Folkman et al., "Seminars in Medicine of the Beth Israel Hospital, Boston: Clinical Applications of Research on Angiogenesis," *The New England Journal of Medicine*, 333(26):1757-1763 (1995).

Folkman et al., "What is the Evidence That Tumors are Angiogenesis Dependent?," *Journal of the National Cancer Institute*, 82(1):4-6 (1990).
Folkman, "New Perspective in Clinical Oncology From Angiogenesis Research," J. Eur. J. Cancer, 32A(4):2534-2539 (1996).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of p-aminosalicylic acid and its salts," International Journal of Pharmaceutics, 126:199-208 (1995).
Formality Requirement dated Jun. 18, 2003 for PH App. Ser. No. 1-2003-500266, 3 pages.
Freshney, R. Ian, "Culture of Animal Cells, A Manual of Basic Technique," Alan R. Liss, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "Mp-412, a dual EGFR/HER2 tyrosine kinase inhibitor: 2. In vivo antitumor effects," Am. Assoc. Cancer Research, A3394, 2005, 2 pages.
Funahashi et al., "P-2123, Lenvatinib treatment of differentiated thyroid cancer (DTC): Analysis to identify biomarkers associated with response," The 71$^{st}$ Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," *J. Clin. Invest.*, 92:1736-1744 (1993).
Furitsu et al., "Stable medicinal compositions of quinolinecarboxamide derivative," Database Caplus Chemical Abstracts Service, Columbus, OH, US (2006) (XP002520305), 11 pages.
Furuta et al., "Synthesis and Biological Evaluation of Selective Inhibitors of PDGF Receptor Auto Phosphorylation," #64, *American Chemical Society, 226$^{th}$ ACS National Meeting*, New York, NY (Sep. 7-11, 2003), 72 pages.
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," *Acta Chimica Hungarica*, 112(2):241-247 (1983).
Gardner et al., "In Vitro Activity Sorghum-Selective Fluorophenyl Urea Herbicides," *Pesticide Biochemistry and Physiology*, 24(3):285-297 (1985).
Gatzemeier et al., "Phase III comparative study of high-dose cisplatin versus a combination of paclitaxel and cisplatin in patients with advanced non-small-cell lung cancer," *J Clin. Oncol.*, 18(19):3390-3399 (2000).
Genitourinary Cancers, Prostate Cancer Genitourinary, http://www.merckmanuals.com/professional/print/sec17/ch241/ch241e.html Mar. 16, 2011, 7 pages.
Giles, "The vascular endothelial growth factor (VEGF) signaling pathway: a therapeutic target in patients with hematologic malignancies," Oncologist, 6(suppl 5):32-39 (2001).
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Golkar et al., "Mastocytosis," Lancet, 349:1379-1385 (1997).
Gould, "Salt Selection for Basic Drugs," *International Journal of Pharmaceutics*, 33:201-217, (1986) (XP025813036), 18 pages.
Grieco et al., "PTC is a Novel Rearranged Form of the ret Proto-Oncogene and Is Frequentrly Detected in Vivo in Human Thyroid Papillary Carcinomas", Cell, 60: 557-563 (1990).

(56) References Cited

OTHER PUBLICATIONS

Guo et al., "Expression of gastric cancer-associated MG7 antigen in gastric cancer, precancerous lesions and H. pylori-associated gastric diseases", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Gura, "Cancer Models Systems for Identifying new drugs are often faulty," Science, 278:1041-1042 (1997).
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Haleblian,"Characterization of habits and crystalline modification of solids and their pharmaceutical applications," *J. Pharm. Sci.*, 64(8):1269-1288 (1975).
Haller, "Chemotherapy for advanced pancreatic cancer," *Int. J. Radiation Oncol. Biol. Phys.*, 56:16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel et al., "The Road Less Travelled: c-kit and Stem Cell Factor," Journal of Neuro-Oncology, 35:327-333 (1997).
Hara et al., "Amplification of c-myc, K-sam, and c-met in Gastric Cancers: Detection by Fluorescence in Situ Hybridization", Laboratory Investigation, 78, 1143-1153, 1998.
Hattori et al., "Immunohistochemical detection of K-sam protein in stomach cancer," *Clin. Cancer Res.*, 2(8):1373-1381 (1996).
Hayek et al., "An in Vivo Model for Study of the Angiogenic Effects of Basic Fibroblast Growth Factor," *Biochemical and Biophysical Research Communications*, 147(2):876-880 (1987).
Haymo et al., "Pericytes in experimental MDA-MB231 tumor angiogenesis," Histochemistry and Cell Biology, 117(6):527-534 (2002) (abstract).
Heinemann, V., et al., "Comparison of the Cellular Pharmacokinetics and Toxicity of . . . 1-beta-d-Arabinofuranosylcytosine", Cancer Research, 48, 4024-4031, 1988.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Heinrich et al., "Inhibition of c-kit receptor tyrosine kinase activity by STI 571, a selective tyrosine kinase inhibitor," *Blood*, 96(3):925-932 (2000) (XP001097629).
Heinrich et al., "Inhibition of KIT tyrosine kinase activity: a novel molecular approach to the treatment of KIT-positive malignancies," *J. Clin. Oncol.*, 20(6):1692-1703 (2002).
Hennequin et al., "Design and Structure-Activity Relationship of a New Class of Potent VEGF Receptor Tyrosine Kinase Inhibitors", Journal of Medicinal Chemistry., 42: 5369-5389, 1999.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.
Hertel LW., et al., "Evaluation of the Antitumor Activity of Gemcitabine (2',2'-Difluoro-2'-deoxycytidine)", Cancer Research, 50, 4417-4422, 1990.
Hibi et al., "Coexpression of the Stem Cell Factor and the c-kit Genes in Small-Cell Lung Cancer," Oncogene, 6:2291-2296 (1991).
Highlights of Prescribing Information: GLEEVEC® (imatinib mesylate) Tablets for Oral Use (Initial U.S. Approval 2001; Label Revised Jan. 2012), 38 pages.
Hines et al., "Coexpression of the c-kit and Stem Cell Factor Genes in Breast Carcinomas," *Cell Growth & Differentiation*, 6:769-779 (1995).
Hogaboam et al., "Novel Role of Transmembrane SCF for Mast Cell Activation and Eotaxin Production in Mast Cell-Fibroblast Interactions," *J. Immunol.*, 160:6166-6171 (1998).

Hon et al., "Suppression of Solid Tumor Growth by Immunoneutralizing Monoclonal Antibody against Human Basic Fibroblast Growth Factor", Cancer Research., 51, 6180-4, 1991.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr. 2005, 2 pages.
Hurwitz et al., "Bevacizumab plus irinotecan, fluorouracil, and leucovorin for metastatic colorectal cancer," N. Engl. J. Med., 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Ikeda et al., "Changes in Phenotype and Proliferative Potential of Human Acute Myeloblastic Leukemia Cells in Culture with Stem Cell Factor," *Experimental Hematology*, 21:1686-1694 (1993).
Ikeda et al., "Expression and Functional Role of the Proto-Oncogene c-kit in Acute Myeloblastic Leukemia Cells," *Blood*, 78(11):2962-2968 (1991).
Inai et al., "Inhibition of vascular endothelial growth factor (VEGF) signaling in cancer causes loss of endothelial fenestrations, regression of tumor vessels, and appearance of basement membrane ghosts," *American Journal of Pathology*, 165:35-52 (2004).
Indian Office Action for App. Ser. No. 1571/CHENP/2007, issued on Oct. 30, 2012, 2 pages.
Indian Office Action for in App. Ser. No. 383/CHENP/2008, issued on May 3, 2012, 2 pages.
Indian Office Action in App. Ser. No. 6415/CHENP/2008, dated Oct. 3, 2013, 2 pages.
Indian Patent Application No. 2572/CHENP/2006 filed Jul. 13, 2006, 1 page.
Information about decision on request for EP App. Ser. No. 06023078.6, dated Mar. 21, 2007, 1 page.
Inoue et al., "Molecular Target Therapy Targeting Angiogenesis Pathways," *The Nishinihon Journal of Urology*, 66:425-432 (2004).
International Preliminary Report on Patentability for International Application No. PCT/JP2010/063804 dated Mar. 13, 2012, 6 pages.
International Preliminary Report on Patentability for International Application No. PCT/JP2007/060560 on Nov. 18, 2008, 6 pages with English translation.
International Preliminary Report on Patentability for International Application No. PCT/JP2006/312487, issued on Dec. 24, 2007, 7 pages.
International Preliminary Report on Patentability for International Application No. PCT/JP2001/09221, dated Jan. 8, 2003, 9 pages.
International Preliminary Report on Patentability for International Application No. PCT/JP2004/003087, issued on Feb. 13, 2006, 5 pages.
International Preliminary Report on Patentability for International Application No. PCT/JP2011/064430, dated Jan. 24, 2013, 6 pages.
International Preliminary Report on Patentability for International Application No. PCT/JP2005/016941, dated on Mar. 20, 2007, 10 pages.
International Preliminary Report on Patentability for International Application No. PCT/JP2003/010964 dated Aug. 10, 2004, 7 pages.
International Preliminary Report on Patentability for International Application No. PCT/JP2007/060560, dated Dec. 10, 2008, 7 pages.
International Preliminary Report on Patentability for International Application No. PCT/JP2009/051244 issued on Aug. 31, 2010, 12 pages (with English translation).
International Preliminary Report on Patentability for International Application No. PCT/JP2008/070321, issued May 11, 2010, 15 pages with English translation.
International Preliminary Report on Patentability for International Application No. PCT/JP2008/051697, issued on Aug. 4, 2009, 18 pages.
International Preliminary Report on Patentability for International Application No. PCT/JP2007/067088 dated Mar. 3, 2009, 16 pages with English translation.

(56) References Cited

OTHER PUBLICATIONS

International Preliminary Report on Patentability for International Application No. PCT/JP2008/051024 dated Jul. 21, 2009, 15 pages with English translation.
International Preliminary Report on Patentability in International Application No. PCT/JP2006/315563 dated Feb. 5, 2008, 10 pp. with English translation.
International Preliminary Report on Patentability in International Application No. PCT/JP2006/315698 dated Feb. 5, 2008, 17 pp. English translation.
International Preliminary Report on Patentability in International Application No. PCT/JP2006/322514 issued on May 7, 2008, 8 pages.
International Preliminary Report on Patentability in International Application No. PCT/JP2006/322516 issued on May 7, 2008, 8 pages.
International Search Report and Written Opinion dated Sep. 14, 2010 for International Application No. PCT/JP2010/063804, 11 pages.
International Search Report dated Apr. 1, 2008 for International Application No. PCT/JP2008/051024, 6 pages.
International Search Report dated Jan. 20, 2009 for International Application No. PCT/JP2008/070321, 8 pages.
International Search Report dated Jan. 23, 2007 for International Application No. PCT/JP2006/322514, 10 pages.
International Search Report dated Jan. 23, 2007 for International Application No. PCT/JP2006/323881, 6 pages.
International Search Report dated Mar. 24, 2009 for International Application No. PCT/JP2009/051244, 6 pages.
International Search Report dated Mar. 4, 2008 for International Application No. PCT/JP2008/051697, 7 pages.
International Search Report dated Nov. 20, 2007 for International Application No. PCT/JP2007/067088, 6 pages.
International Search Report dated Oct. 17, 2006 for International Application No. PCT/JP2006/315698, 5 pages.
International Search Report dated Sep. 11, 2007 for International Application No. PCT/JP2007/060560, 6 pages.
International Search Report dated Sep. 4, 2007 for International Application No. PCT/JP2007/063525, 7 pages.
International Search Report dated Sep. 5, 2006 for International Application No. PCT/JP2006/315563, 2 pages.
International Search Report for International Application No. PCT/JP2001/09221, issued on Jan. 15, 2002, 9 pages.
International Search Report for International Application No. PCT/JP2006/317307, issued on Dec. 12, 2006, 3 pages.
International Search Report for International Application No. PCT/JP2004/003087, issued on Jul. 13, 2004, 3 pages.
International Search Report for International Application No. PCT/JP2005/016941, dated on Nov. 15, 2005, 4 pages.
International Search Report in International Application No. PCT/JP2006/322516 issued on Jan. 23, 2007, 5 pages.
Invitation to declare maintenance of the application for EP App. Ser. No. 01976786.2, dated Jul. 12, 2004, 1 page.
Invitation to declare maintenance of the application for EP App. Ser. No. 05783232.1, dated Sep. 25, 2007, 1 page.
Invitation to declare maintenance of the application for EP App. Ser. No. 06023078.6, dated May 2, 2007, 1 page.
Israel 200090 Office Actions issued on Jun. 22, 2010, 3 pages (with English translation).
Israel 200090 Response to Office Action filed on Oct. 12, 2010, 3 pages.
Israel Appl. No. 195282 IDS List filed on Jul. 1, 2010, 3 pages.
Israel Office Action directed at Appl. No. 195282 issued on Jan. 26, 2010, 4 pages with English translation.
Israel Office Action directed at Appl. No. 205512 issued on Nov. 13, 2011, 4 pages with English translation.
Israel Response (IDS List) to Office Action directed at Appl. No. 195282 filed on May 3, 2010, 6 pages with English translation.
Israeli Office Action dated Mar. 27, 2012 for Israeli Application No. 189589, 3 pages with English translation.
Israeli Office Action for App. Ser. No. 155447, issued on Oct. 16, 2007, 3 pages (with English translation).
Israeli Office Action for App. Ser. No. 189677, issued on Feb. 18, 2009, 2 pages (with English translation).
Israeli Office Action for App. Ser. No. 195282, issued on Feb. 5, 2012, 3 pages (with English translation).
Israeli Office Action for App. Ser. No. 199907, issued on Apr. 22, 2012, 3 pages (with English translation).
Israeli Office Action issued on May 16, 2010 for corresponding Israeli Application No. 189589, 3 pages with English translation.
Itoh et al., "Preferential alternative splicing in cancer generates a K-sam messenger RNA with higher transforming activity," *Cancer Res.*, 54:3237-3241 (1994).
Jakeman et al., "Developmental Expression of Binding Sites and Messenger Ribonucleic Acid for Vascular Endothelial Growth Factor Suggests a Role for This Protein in Vasculogenesis and Angiogenesis," *Endocrinology*, 133(2):848-859 (1993).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Allowance for App. Ser. No. P2005-515330, issued on Apr. 21, 2009, 2 pages.
Japanese Allowance for App. Ser. No. P2005-516605, issued on Dec. 7, 2010, 5 pages (with English translation).
Japanese Classification of Gastric Carcinoma "Igan-Toriatsukai Kiyaku" (Jun. 1999, 13th ed.) and an English translation, 10 pages.
Japanese Decision to Grant A Patent dated Jan. 30, 2013 for Japanese Application No. 2007-533350, 3 pages with English translation.
Japanese Notice of Reasons for Rejection dated May 15, 2012 for Japanese Application No. 2007-533350, 6 pages with English translation.
Japanese Office Action dated Apr. 11, 2005 for App. Ser. No. 2002-536056, 6 pages (with English translation).
Japanese Office Action for App. Ser. No. 2007-522356, issued on Feb. 8, 2011, 5 pages.
Japanese Office Action for App. Ser. No. P2005-516605, issued on Nov. 4, 2009, 7 pages.
Japanese Office Action for App. Ser. No. P2008-516724, issued on Oct. 9, 2012, 6 pages (with English translation).
Jhiang, "The RET proto-oncogene inn human cancers," *Oncogene*, 19:5590-5597 (2000).
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," *J. Clin. Endocrinol. Metab.*, 89:4142-4145 (2004).
Joao et al., "Somatic trinucleotide change encompassing codons 882 and 883 of the RET protooncogene in a patient with sporadic medullary thyroid carcinoma", European Journal of Endocrinology, 142,573-575, (2000).
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Paclitaxel plus carboplatin in advanced non-small-cell lung cancer: a phase II trial," *J. Clin. Oncol.*, 14(7):2054-2060 (1996).
Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.
Jung et al., "Effects of combination anti-vascular endothelial growth factor receptor and anti-epidermal growth factor receptor therapies on the growth of gastric cancer in a nude mouse model," *Eur. J Cancer*, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," *Ann Rheum. Dis.*, 64:1126-1131 (2005).

(56) References Cited

OTHER PUBLICATIONS

Kanai et al., "Development Status and Future Prospects of Novel Molecular Target Drugs for Hepatocellular Carcinoma", Journal of the Japanese Society of Gastroenterology, 106:1727-1735 (2009).

Kanai et al., "Current status and future perspective of molecular targeted therapy for hepatocellular carcinoma," *Journal of the Japanese Society of Gastroenterology*, 106:1727-1735 (2009) (English translation).

Kanakura et al., "Expression, Function and Activation of the Proto-Oncogene c-kit Product in Human Leukemia Cells," *Leukemia and Lymphorma*, 10:35-41 (1993).

Kashuk et al., "Phenotype-genotype correlation in Hirschsprung disease is illuminated by comparative analysis of the RET protein sequence," PNAS, 102(25):8949-8954 (2005).

Kawano et al., "Presentation Abstract, Abstract No. 1619, Combination of VEGFR inhibitor lenvatinib (E7080) and Met/EphB4 inhibitor golvatinib (E7050) overcomes VEGFR inhibitor—resistant tumor vascular", Annual Meeting 2013, Walter E. Washington Convention Center, Washington, D.C., Apr. 6-10, 2013, 1 page.

Kay et al., "Eosinophils and Eosinophil-Associated Cytokines in Allergic Inflammation," *Int. Arch. Allergy Immunol.*, 113:196-199 (1997).

Kelly et al., "Randomized phase III trial of paclitaxel plus carboplatin versus vinorelbine plus cisplatin in the treatment of patients with advanced none—small-cell lung cancer: a Southwest Oncology Group trial," *J. Clin. Oncol.*, 19(13):3210-3218 (2001).

Kibbe, Handbook of Pharmaceutical Excipients. Third Edition, 2000, pp. 6-1 through 6-6.

Kim et al., "RET Oligonucleotide Microarray for the Detection of RET Mutations in Multiple Endocrine Neoplasia Type 2 Syndromes", Clinical Cancer Research, 8,457-463, (2002).

Kim et al., "A phase II study of irinotecan plus cisplatin for patients with advanced stage IIIB or IV NSCLC previously treated with nonplatinum-based chemotherapy," *Cancer*, 107(4):799-805 (2006).

Kim et al., "An orally administered multitarget tyrosine kinase inhibitor, SU11248, is a novel potent inhibitor of thyroid oncogenic RET/papillary thyroid cancer kinases," *J Clin. Endocrinol. Metlab.*, 91(10):4070-4076 (2006).

Kim, "Technology evaluation: Matuzumab, Merck KGaA", Curr Opin Mol Ther. 2004; 6(1):96-103.

Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.

Kitamura et al., "Regulation of Development, Survival and Neoplastic Growth of Mast Cells through the c-kit Receptor," *Int. Arch Allergy Immunol.*, 107:54-56 (1995).

Kitteringham et al., "A Simple Method for the Synthesis of Unsymmetrical Ureas," *Synthetic Communications*, 30(11):1937-1943 (2000).

Kleespies et al., "Tyrosine kinase inhibitors and gemcitabine: New treatment options in pancreatic cancer,?" *Drug Resistance Updates*, 9:1-18 (2006).

Klugbauer and Rabes, "The transcription coactivator HT1 Fl and a related protein are fused to the RET receptor tyrosine kinase in childhood papillary thyroid carcinomas", Oncogene, 18: 4388-4393(1999).

Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).

Klugbauer et al., "Detection of a Novel Type of RET Rearrangement (PTC5) in Thyroid Carcinomas after Chernobyl and Analysis of the Involved RET-fused Gene RFG5", Cancer Research, 58:198203 (1998).

Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.

Kolibaba et al., "Protein Tyrosine Kinases and Cancer," *Biochimica et Biophysica Acta*, 1333:F217-F248 (1997).

Korean ("KR") Notice of Allowance issued on Aug. 25, 2010 corresponding KR Application No. 10-2008-7005195, 3 pages with English translation.

Korean ("KR") Office Action issued on Dec. 24, 2009 for corresponding KR Application No. 10-2008-7005195, 7 pages with English translation.

Korean ("KR") Office Action issued on May 29, 2010 for corresponding KR Application No. 10-2008-7005195, 6 pages with English translation.

Korean Office Action for App. Ser. No. 10-2003-7005506, issued on Jan. 5, 2006, 5 pages (with English translation).

Korean Office Action for App. Ser. No. 10-2005-7020292, issued on Dec. 8, 2005, 5 pages (with English translation).

Korean Office Action for App. Ser. No. 10-2007-7001347, issued on Apr. 27, 2012, 6 pages (with English translation).

Korean Office Action for App. Ser. No. 10-2009-7005657, issued on Sep. 30, 2013, 27 pages (with English translation).

Korean Office Action in KR App. Ser. No. 10-2008-7029472, dated Sep. 30, 2013, 27 pages (with English translation).

Kotva et al., "Substances with Antineoplastic Activity, LIII. N-(δ-(4-Pyrrolo[2,3-d]Pyrimidinylthio) Valeryl] } Amino Acids and Analogous Derivatives of Di-and Triglycine," Collection Czechoslov. Chem. Commun., 38:1438-1444 (1973).

Koyama et al, "Anti-tumor effect of E7080, a novel angiogenesis inhibitor," Folia Pharmacol. Japan., 2008, 132: 100-104 (with English translation).

Kruckeberg et al., "Pyrosequencing Technology as a Method for the Diagnosis of Multiple Endocrine Neoplasia Type 2", Clinical Chemistry, 50, 522-529, 2004.

Krystal et al., "Indolinone Tyrosine Kinase Inhibitors Block Kit Activation and Growth of Small Cell Lung Cancer Cells", Cancer Research., 61, 3660-3668, 2001.

Kubo et al., "A novel series of 4-phenoxyquinolines: potent and highly selective inhibitors of pdgf receptor autophosphorylation", Bioorganic and Medicinal Chemistry Letters., 7, 2935-2940, 1997.

Kubo et al., "Novel Potent Orally Active Selective VEGFR-2 Tyrosine Kinase Inhibitors: . . . ureas", Journal of Medicinal Chemistry., 48, 1359-1366, 2005.

Kumar et al., "Discovery and biological evaluation of GW654652: A pan inhibitor of VEGF receptors," Proceedings of the American Association for Cancer Research, 44, 9, (Abstract 39), 2003, 2 pages.

Laird et al., "SU6668 Is a Potent Antiangiogenic and Antitumor Agent That Induces Regression of Established Tumorsl", Cancer Research., 60, 4152-4160, 2000.

Lam et al., "High prevalence of RET proto-oncogene activation (RET/PTe) in papillary thyroid carcinomas", Eur J Endocrinology, 147: 741-745 (2002).

Lasota et al., "Mutations in Exons 9 and 13 of KIT Gene Are Rare Events in Gastrointestinal Stromal Tumors," American Journal of Pathology, 157(4):1091-1095 (2000).

LeDoussal et al. "Bispecific-antibody-mediated targeting of radiolabeled bivalent haptens: theoretical, experimental and clinical results", Int. J. Cancer Suppl. 7: 58-62, 1992.

Lee et al., "In vivo Target Modulation and Biological Activity of CHIR-258, a Multitargeted Growth Factor Receptor Kinase Inhibitor, in Colon Cancer Models", Clinical Cancer Research., 11, 3633-3641, 2005.

Lennartsson et al., The Stem Cell Factor Receptor/c-Kit as a Drug Target in Cancer, *Current Cancer Drug Targets*, 6:561-571 (2006).

Lesueur et al., "Polymorphisms in RET and its coreceptors and ligands as genetic modifiers of multiple endocrine neoplasia type 2A," *Cancer Res.*, 66:1177-1180 (2006).

Leukemias, Hematology, and Oncology, http://www.merkmanuals.com/professional/print/sec11/ch142a.html Mar. 16, 2011, 5 pages.

Lev et al., "A Specific Combination of Substrates is Involved in Signal Transduction by the Kit-Encoded Receptor," *The EMBO Journal*, 10(3):647-654 (1991).

Li et al., "Abrogation of c-kit/Steel factor-dependent tumorigenesis by kinase defective mutants of the c-kit receptor: c-kit kinase defective mutants as candidate tools for cancer gene therapy," *Cancer Res.*, 56:4343-4346 (1996) (XP002522473).

Li et al., "ABT-869 a novel multi-targeted receptor tyrosine kinase inhibitor: characterization of FLT3 phosphorylation in a model of

(56) References Cited

OTHER PUBLICATIONS acute myelogenous leukemia," AACR American Association Cancer Research, 96th Annual Meeting, 46:1407, (Abstract 5981), Anaheim, Orange County CA USA Apr. 16-20, 2005, 2 pages.
Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026 (2002).
Liu et al., "Structure of Human Methionine Aminopeptidase-2 Complexed with Fumagillin", Science., 282, 1324-1327, 1998.
Logie et al., "Activating mutations of the tyrosine kinase receptor FGFR3 are associated with benign skin tumors in mice and humans," Human Mol. Genet., 14:1153-1160 (2005).
Longley et al., "Altered Metabolism of Mast-Cell Growth Factor (c-kit Ligand) in Cutaneous Mastocytosis," *The New England Journal of Medicine*, 328(18):1302-1307 (1993).
Longley et al., "Classes of c-KIT activating mutations: proposed mechanisms of action and implications mplications for disease classification and therapy," *Leuk. Res.*, 25:571-576 (2001).
Longley et al., "Somatic c-KIT Activating Mutation in Urticaria Pigmentosa and Aggressive Mastocytosis: Establishment of Clonality in a Human Mast Cell Neoplasm," *Nature Genetics*, 12:312-314 (1996).
Lukacs et al., "Stem Cell Factor (c-kit Ligand) Influences Eosinophil Recruitment and Histamine Levels in Allergic Airway Inflammation," *J. Immunol.*, 156:3945-3951 (1996).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Maintenance of the application for EP App. Ser. No. 01976786.2, dated Sep. 6, 2004, 1 page.
Maintenance of the application for EP App. Ser. No. 05783232.1, dated Nov. 9, 2007, 1 pages.
Maintenance of the application for EP App. Ser. No. 06023078.6, dated Jun. 19, 2007, 1 page.
Masferrer et al., "COX-2 Inhibitors A New Class of Antiangiogenic Agents", Annals of N.Y. Acad. Science., 889:84-6, 1999.
Matsui et al., "E7080 (ER-203492-00), a Novel VEGF Receptor Tyrosine Kinase Inhibitor-I. Characterization as an Angiogenesis Inhibitor," Abstract # 51, *AACR*, Washington, USA (Jul. 11-14 2003).
Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9 2003).
Matsui et al., "E7080, a novel inhibitor that targets multiple kinases, has potent antitumor activities against stem cell factor producing human small cell lung cancer H146, based on angionenesis inhibition," *Int. J Cancer*, 122:664-671 (2008).
Matsui et al., "E7080, a novel multi-receptor Tyrosine Kinase Inhibitor, inhibited in vitro / in vivo VEGF- and SCF-driven angiogenesis SCLC cell line," Abstract #146, *EORTC-NCI-AACR*, Geneva, Switzerland (Sep. 28-Oct. 1, 2004).
Matsui et al., "E7080, a novel multi-targeted tyrosine kinase inhibitor, exhibits anti-angiogenic activity via inhibition of KIT signaling in a small cell lung cancer xenograft model," *Eur. J. Cancer*, 2(8):47 (2004).
Matsui et al., "Quantitative analysis of the profile of tumor vessels may be useful as predictive biomarkers for E7080," Abstract #4631, *98th AACR annual meeting*, Los Angeles, CA, (Apr. 14-18, 2007).
Matsui et al., "VEGFRs inhibitor E7080 inhibits lymph node metastasis of human breast carcinoma, by preventing murine lymphatic endothelial cells from lymphangiogenesis," Abstract #PD12-8, *18th EORTC-NCI-AACR Symposium on "Molecular Targets and Cancer Therapeutics,"* Prague, Czech Republic (Nov. 7-10, 2006).
Matsui, "Extracellular matrix of linitis plastica as a possible new therapeutic target," Surgical Treatment, Sep. 2003, 89(3):301-306 (with English translation.
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," Mol. Cancer Ther., 3(9):1041-1048 (2004).
McCulloch et al., "Astragalus-based Chinese herbs and platinum-based chemotherapy for advanced non-small-cell lung cancer: meta-analysis of randomized trials," *J Clin. Oncol.*, 24(3):419-430 (2006).
Meltzer, "The Pharmacological Basis for the Treatment of Perennial Allergic Rhinitis and Non-Allergic Rhinitis with Topical Corticosteroids," *Allergy*, 52:33-40 (1997).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," *Clin. Cancer Res.*, 9:327-337 (2003).
Metcalfe et al., "Lineage Commitment in the Progeny of Murine Hematopoietic Preprogenitor Cells: Influence of Thrombopoietin and Interleukin 5," *Proc. Nat'l Acad. Sci. USA*, 95:6408-6412 (1998).
Metcalfe et al., "Mast cells," *Physiol. Rev.*, 77(4):1033-1079 (1997).
Metcalfe, "Classification and Diagnosis of Mastocytosis: Current Status," *J. Invest. Dermatol.*, 96:2S-4S (1991).
Mexican Office Action in App. Ser. No. MX/a/2010/008187, dated Aug. 21, 2013, 6 pages (with English translation).
Micke et al., "Characterization of c-kit expression in small cell lung cancer: prognostic and therapeutic implications," *Clin. Cancer Res.*, 9:188-194 (2003).
Miknis et al., "AARY-334543, a potent, orally active small molecule inhibitor of EGFR and ErbB2," Am. Assoc. Cancer Res. Abstract 3399, 2005, 2 pages.
Miller et al., "Paclitaxel plus bevacizumab versus paclitaxel alone for metastatic breast cancer," *N. Engl. J Med.*, 357(26):2666-2676 (2007).
Milstein and Cuello, "Hybrid hybridomas and their use in immunohistochemistry", Nature 305: 537-9, 1983.
Mitchell al, "The influence of additives on the cloud point, disintegration and dissolution of hydroxypropylmethylcellulose gels and matrix tablets," International Journal of Pharmaceutics, 1990, vol. 66, No. 1/3, pp. 233-242.
Miyauchi et al., "Two Germline Missense Mutations of Co dons 804 and 806 of the RET protooncogene in the Same 15 Allele in a Patient with Multiple Endocrine Neoplasia Type 2B without Codon 915 Mutation", Japanese Journal of D Cancer Research, 90, 1-5, (1999).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003), 1 page.
Mohammadi et al., "Crystal structure of an angiogenesis inhibitor bound to the FGF receptor tyrosine kinase domain", EMBO J., 17, 5896-5904, 1998.
Mologni et al., "Inhibition of RET tyrosine kinase by SU5416," *J. Mol. Endocrinol.*, 37(2):199-212 (2006).
Morgan et al., "Dynamic contrast-enhanced magnetic resonance imaging as a biomarker for the pharmacological response of PTK787/Zk 222584, an inhibitor of the vascular endothelial growth factor receptor tyrosine kinases, in patients with advanced colorectal cancer and liver metastases: results from two phase I studies," *J. Clin. Oncol.*, 21(21):3955-3964 (2003).
Morikawa et al., "Angiogenesis and Pericytes, " *The Cell*, 37(4):164-168 (2005) (English translation).
Morris et al., "An Integrated Approach to the Selection of optimal Salt Form for a New Drug Candidate," *International Journal of Pharmaceutics*, 105:209-217 (1994) (XP023724810).
Myers et al., "The Preparation and SAR of 4-(Anilino), 4-(Phenoxy), and 4-(Thiophenoxy)-Quinazolines: Inhibitors of p561ck and EGF-R Tyrosine Kinase Activity," *Bioorgan. & Med. Chem. Letters*, 7:417-420 (1997).
Naclerio et al., "Rhinitis and Inhalant Allergens," JAMA, 278(22):1842-1848 (1997).
Nagata et al., "Elevated Expression of the Proto-Oncogene c-kit in Patients with Mastocytosis," *Leukemia*, 12:175-181 (1998).

(56) References Cited

OTHER PUBLICATIONS

Nakamura et al., "KRN633: A Selective inhibitor of vascular endothelial growth factor receptor-2 tyrosine kinase that suppresses tumor angiogenesis and growth", Molecular Cancer Therapeutics., 2004, 3:1639-49.
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, *AACR*, Toronto, Canada (Apr. 5-9, 2003).
Nakamura et al., "In vitro selectivity and potency of KRN951, a novel inhibitor of VEGF receptor tyrosine kinases," Proceedings of the American Association for Cancer Research, 45, 594, (Abstract 2571), 2004, 1 page.
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," *Int. J. Cancer*, 98:310-315 (2002).
Naski et al., "Graded activation of fibroblast growth factor receptor 3 by mutations causing achondroplasia and thanatophoric dysplasia," *Nat. Genet.*, 13:233-237 (1996).
Natali et al., "Breast Cancer is Associated with Loss of the c-kit Oncogene Product," *Int. J. Cancer*, 52:713-717 (1992).
NCBI GenBank Accession No. NM_000222, Coffey et al. (Feb. 11, 2008), 7 pages.
Nishikawa et al., "Cys611Ser mutation in RET proto-oncogene in a kindred with medullary thryroid carcinoma and Hirschsprung's disease", European Journal of Human Genetics, 11,364-368 (2003).
Nishio et al, "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," *Cold Spring Harbor Laboratory Press*, 3:816-826 (1989) (XP002522472).
Non-Final Office Action in U.S. Appl. No. 10/577,531, mailed Sep. 23, 2008, 17 pages.
Non-Final Office Action in U.S. Appl. No. 10/797,903, mailed Aug. 20, 2009, 10 pages.
Non-Final Office Action in U.S. Appl. No. 10/797,903, mailed Dec. 11, 2007, 12 pages.
Noriyuki et al., "Anti-tumor effect of E7080, a novel angiogenesis inhibitor," Database BIOSIS [Online] Biosciences Information Service, Philadelphia, PA, US: Database accession No. PREV200800475929, Aug. 2008, XP002677323, 1 page.
Notice of Acceptance dated Aug. 10, 2004 for ZA Patent App. No. 2003/3567, 1 page.
Notice of Acceptance dated Aug. 3, 2006 for AU App. Ser. No. 2001295986, 4 pages.
Notice of Acceptance dated May 13, 2008 for AU App. Ser. No. 2006236039, 4 pages.
Notice of Acceptance for AU App. Ser. No. 2009210098, dated Jun. 4, 2013, 3 pages.
Notice of Acceptance of Complete Specification dated Mar. 4, 2005 for NZ App. Ser. No. 525324, 1 page.
Notice of Allowability dated Nov. 28, 2007 for PH App. Ser. No. 1-2003-500266, 1 page.
Notice of Allowance dated Apr. 19, 2005 for RU App. Ser. No. 2003114740, 79 pages (with English translation).
Notice of Allowance dated Apr. 19, 2011 for JP App. Ser. No. 2007-522356, 5 pages.
Notice of Allowance dated Apr. 24, 2012 for U.S. Appl. No. 12/524,754, 10 pages.
Notice of Allowance dated Apr. 29, 2010 for AU App. Ser. No. 2005283422, 3 pages.
Notice of Allowance dated Aug. 2, 2005 for JP App. Ser. No. 2002-536056, 2 pages (with English translation).
Notice of Allowance dated Aug. 7, 2012 for Japanese App. Ser. No. P2007-529565, 6 pages (with English translation).
Notice of Allowance dated Dec. 15, 2006 for CN App. Ser. No. 01819710.8, 4 pages.
Notice of Allowance dated Dec. 26, 2007 for IL App. Ser. No. 155447, 2 pages (with English translation).
Notice of Allowance dated Feb. 15, 2013 for NZ App. Ser. No. 598291, 1 page.
Notice of Allowance dated Feb. 27, 2009 for U.S. Appl. No. 11/293,785, 4 pages.
Notice of Allowance dated Feb. 5, 2010 for CN App. Ser. No. 200580026468.7, 5 pages (with English translation).
Notice of Allowance dated Jul. 17, 2012 for JP App. Ser. No. P2011-527665, 4 pages (with English translation).
Notice of Allowance dated Jul. 21, 2009 for JP App. Ser. No. 2005-124034, 6 pages (with English translation).
Notice of Allowance dated Jun. 13, 2006 for U.S. Appl. No. 10/420,466, 2 pages.
Notice of Allowance dated Jun. 20, 2012 for EP App. Ser. No. 06782407.8, 35 pages.
Notice of Allowance dated Jun. 25, 2012 for EP App. Ser. No. 07806561.2, 7 pages.
Notice of Allowance dated Jun. 3, 2008 for U.S. Appl. No. 11/293,785, 6 pages.
Notice of Allowance dated Mar. 14, 2010 for IL App. Ser. No. 189677, 3 pages (with English translation).
Notice of Allowance dated Mar. 16, 2007 for U.S. Appl. No. 10/420,466, 3 pages.
Notice of Allowance dated Mar. 22, 2012 for U.S. Appl. No. 12/986,638, 12 pages.
Notice of Allowance dated Mar. 8, 2013 for CA App. Ser. No. 2627598, 1 page.
Notice of Allowance dated May 18, 2009 for U.S. Appl. No. 11/293,785, 4 pages.
Notice of Allowance dated May 6, 2013 for EP App. Ser. No. 04818213.3, 22 pages.
Notice of Allowance dated Nov. 14, 2011 for IL App. Ser. No. 181697, 4 pages (with English translation).
Notice of Allowance dated Nov. 19, 2008 for U.S. Appl. No. 11/293,785, 4 pages.
Notice of Allowance dated Nov. 2, 2012 for EP App. Ser. No. 06782407.8, 2 pages.
Notice of Allowance dated Nov. 2, 2012 for EP App. Ser. No. 07806561.2, 2 pages.
Notice of Allowance dated Oct. 14, 2010 for CA App. Ser. No. 2426461, 1 page.
Notice of Allowance dated Oct. 17, 2011 for CA App. Ser. No. 2579810, 1 page.
Notice of Allowance dated Oct. 18, 2006 for MX App. Ser. No. PA/a/2003/003362, 4 pages (with English translation).
Notice of Allowance dated Oct. 20, 2008 for TW App. Ser. No. 90125928, 4 pages (with English translation).
Notice of Allowance dated Oct. 31, 2008 for NO App. Ser. No. 20031731, 4 pages (with English translation).
Notice of Allowance dated Oct. 9, 2010 for CN App. Ser. No. 200710007097.9, 4 pages (with English translation).
Notice of Allowance dated Sep. 12, 2005 for U.S. Appl. No. 10/420,466, 2 pages.
Notice of Allowance dated Sep. 20, 2011 for JP App. Ser. No. 2006-535174, 4 pages.
Notice of Allowance dated Sep. 25, 2012 for U.S. Appl. No. 12/986,638, 56 page.
Notice of Allowance dated Sep. 4, 2012 in JP App. Ser. No. P2009-123432, 5 pages (with English translation).
Notice of Allowance for CN App. Ser. No. 200980103218.7, dated May 27, 2013, 4 pages (with English translation).
Notice of Allowance for JP App. Ser. No. 2008-516724, dated Jan. 22, 2013, 4 pages, with English translation.
Notice of Allowance for JP App. Ser. No. P2008-532141, dated Sep. 10, 2013, 5 pages (with English translation).
Notice of Allowance for U.S. Appl. No. 12/524,754, dated Jan. 18, 2013, 9 pages.

(56) References Cited

OTHER PUBLICATIONS

Notice of Allowance for U.S. Appl. No. 12/741,682, dated Feb. 19, 2013, 65 pages.
Notice of Allowance for U.S. Appl. No. 12/741,682, dated Jun. 19, 2013, 10 pages.
Notice of Allowance for U.S. Appl. No. 12/524,754 dated Oct. 9, 2012, 36 pages.
Notice of Allowance for U.S. Appl. No. 11/997,719, dated Sep. 13, 2013, 20 pages.
Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in EP App. Ser. No. 04818213.3, dated Sep. 19, 2013, 2 pages.
Notice of Allowance in U.S. Appl. No. 12/741,682, dated Oct. 21, 2013, 12 pages.
Notice of Allowance in U.S. Appl. No. 13/624,278, dated Sep. 16, 2013, 20 pages.
Notice of Allowance issued in CN App. Ser. No. 200880115011.7, dated Aug. 5, 2013, 4 pages (with English translation).
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 40 pages.
Notice of Allowance issued in IL App. Ser. No. 175363, dated Aug. 13, 2013, 2 pages (with English translation).
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.
Notice of decision for patent dated Apr. 17, 2006 for KR App. Ser. No. 10-2005-7020292, 4 pages (with English translation).
Notice of decision for patent dated Jun. 12, 2006 for KR App. Ser. No. 10-2003-7005506, 4 pages (with English translation).
Notice of Reasons for Rejection issued in JP App. Ser. No. P2009-540099, dated Jul. 2, 2013, 7 pages (with English translation).
Notice of Reasons for Rejection mailed on Nov. 13, 2012 issued for corresponding Japanese Application No. 2007-533350, 3 pages with full English language translation.
Notice Prior to Examination dated Jun. 29, 2008 for IL App. Ser. No. 189677, 3 pages (with English translation).
Notice Prior to Examination dated Mar. 9, 2009 for IL App. Ser. No. 181697, 3 pages (with English translation).
Notice Requesting Submission of Opinion in KR Application No. 10-2006-7013993 mailed Jul. 31, 2007, 9 pages (with English translation).
Notification dated Apr. 25, 2008 for PH App. Ser. No. 1-2003-500266, 1 page.
Notification of Defects for IL App. Ser. No. 195282, dated Apr. 10, 2013, 4 pages (with English Translation).
Nugiel et al., "Synthesis and evaluation of indenopyrazoles as cyclin-dependent kinase inhibitors. 2. Probing the indeno ring substituent pattern," *J. Med. Chem.*, 45(24):5224-5232 (2002).
Nyati et al., "Radiosensitization by Pan ErbB Inhibitor CI-1033 in Vitro and in Vivo", Clinical Cancer Research., 10:691-700, 2004.
Ocqueteau et al., Expression of the CD117 antigen (C-Kit) on normal and myelomatous plasma cells, Br. J. Haematol., 95:489-493 (1996).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 27, 2010 for CN App. Ser. No. 200710007097.9, 7 pages (with English translation).
Office Action dated Apr. 28, 2009 for JP App. Ser. No. 2005-124034, 3 pages (with English translation).
Office Action dated Apr. 8, 2013 for U.S. Appl. No. 11/997,719, 55 pages.
Office Action dated Apr. 9, 2013 for CN App. Ser. No. 201080030508.6, 6 pages (with English translation).
Office Action dated Aug. 11, 2006 for CN App. Ser. No. 01819710.8, 6 pages (with English translation).
Office Action dated Aug. 8, 2003 for PH App. Ser. No. 1-2003-500266, 1 page.
Office Action dated Dec. 20, 2010 for IL App. Ser. No. 181697, 3 pages (with English translation).
Office Action dated Dec. 25, 2009 for CN App. Ser. No. 200710007097.9, 6 pages (with English translation).
Office Action dated Feb. 10, 2006 for CN App. Ser. No. 01819710.8, 8 pages (with English translation).
Office Action dated Jan. 27, 2009 for JP App. Ser. No. 2005-124034, 8 pages (with English translation).
Office Action dated Jul. 15, 2011 for CA App. Ser. No. 2579810, 2 pages.
Office Action dated Jul. 21, 2006 for PH App. Ser. No. 1-2003-500266, 1 pages.
Office Action dated Jul. 24, 2009 for CN App. Ser. No. 200710007096.4, 8 pages (with English translation).
Office Action dated Jul. 27, 2005 for KR App. Ser. No. 10-2003-7005506, 4 pages (with English translation).
Office Action dated Jun. 26, 2009 for CN App. Ser. No. 200580026468.7, 25 pages (with English translation).
Office Action dated Jun. 27, 2007 for PH App. Ser. No. 1-2003-500266, 1 page.
Office Action dated Jun. 5, 2012 for JP App. Ser. No. 2009-123432, 4 pages (with English translation).
Office Action dated Jun. 7, 2006 for MX App. Ser. No. PA/a/2003/003362, 6 pages (with English translation).
Office Action dated Mar. 14, 2013 for CN App. Ser. No. 200780017371.9, 9 pages (with English translation).
Office Action dated Mar. 21, 2007 for PH App. Ser. No. 1-2003-500266, 1 page.
Office Action dated Mar. 29, 2013 for U.S. Appl. No. 13/624,278, 73 pages.
Office Action dated Mar. 7, 2007 for NO App. Ser. No. 20031731, 3 pages (with English translation).
Office Action dated May 13, 2005 for CN App. Ser. No. 01819710.8, 8 pages (with English translation).
Office Action dated May 16, 2008 for NO App. Ser. No. 20031731, 2 pages (with English translation).
Office Action dated Nov. 13, 2012 for JP App. Ser. No. P2008-532141, 8 pages (with English translation).
Office Action dated Nov. 20, 2009 for CN App. Ser. No. 200580026468.7, 9 pages (with English translation).
Office Action dated Nov. 26, 2007 for MX App. Ser. No. PA/a/2005/013764, 6 pages (with English translation).
Office Action dated Oct. 11, 2007 for TW App. Ser. No. 90125928, 5 pages (with English translation).
Office Action dated Oct. 15, 2012 for IL App. Ser. No. 200090, 5 pages (with English translation).
Office Action dated Oct. 15, 2012 for NZ App. Ser. No. 598291, 2 pages.
Office Action dated Oct. 4, 2005 for MX App. Ser. No. PA/a/2003/003362, 8 pages (with English translation).
Office Action dated Oct. 4, 2007 for NO App. Ser. No. 20031731, 2 pages (with English translation).
Office Action dated Sep. 11, 2009 for CN App. Ser. No. 200710007097.9, 8 pages (with English translation).
Office Action dated Sep. 19, 2012 for CA App. Ser. No. 2627598, 3 pages.
Office Action dated Sep. 28, 2011 for KR App. Ser. No. 10-2007-7001347, 12 pages (with English translation).
Office Action dated Sep. 28, 2012 for CN App. Ser. No. 200780017371.9, 9 pages (with English translation).
Office Action dated Sep. 29, 2012 for CN App. Ser. No. 200980103218.7, 13 pages (with English translation).
Office Action dated Sep. 5, 2008 for NO App. Ser. No. 20031731, 2 pages (with English translation).

(56) References Cited

OTHER PUBLICATIONS

Office Action dated Sep. 5, 2012 for CN App. Ser. No. 200880003336.6, 12 pages (with English translation).
Office Action dated Sep. 5, 2012 for CN App. Ser. No. 200880115011.7, 6 pages (with English translation).
Office Action dated Sep. 7, 2007 for PH App. Ser. No. 1-2003-500266, 1 page.
Office Action directed at Israel Application No. 207089 issued on Nov. 13, 2011, 4 pages (with English translation).
Office Action for Canadian Application No. 2,620,594, dated Aug. 15, 2011, 2 pages.
Office Action for EP App. Ser. No. 08846814.5, dated Apr. 16, 2013, 5 pages.
Office Action for IL 199907 issued on Jun. 17, 2010, 3 pages with English translation.
Office Action for IL App. Ser. No. 175363, dated Jan. 2, 2013, 2 pages, with English translation.
Office Action for IL App. Ser. No. 200090, dated Jul. 24, 2013, 5 pages (with English translation).
Office Action for IL App. Ser. No. 205512, dated Dec. 20, 2012, 8 pages, with English translation.
Office Action for IL App. Ser. No. 207089, dated Jan. 6, 2013, 5 pages (with English translation).
Office Action for Indian Application No. 1908/DELNP/2008, dated Feb. 2, 2012, 2 pages.
Office Action for JP App. Ser. No. 2008-556208, dated Jan. 22, 2013, 8 pages, with English translation.
Office Action for JP App. Ser. No. P2008-532141, dated May 21, 2013, 4 pages (with English translation).
Office Action for JP App. Ser. No. P2009-551518, dated Jun. 18, 2013, 5 pages (with English translation).
Office Action for JP2007-542863 dated May 29, 2012, 8 pages with English translation.
Office Action for KR App. Ser. No. 10-2008-7013685, dated May 20, 2013, 10 pages (with English translation).
Office Action for PH App. Ser. No. 1-2011-502441 on Oct. 1, 2013, 1 page.
Office Action for U.S. Appl. No. 12/039,381, dated Sep. 12, 2013, 15 pages.
Office Action for U.S. Appl. No. 13/083,338, dated Jan. 3, 2013, 9 pages.
Office Action for U.S. Appl. No. 13/238,085, dated Sep. 6, 2013, 10 pages.
Office Action for U.S. Appl. No. 12/439,339, dated May 23, 2013, 15 pages.
Office Action in Chinese Application No. 200710007097.9, mailed Mar. 6, 2009, 5 pages.
Office Action in JP Application No. P2005-516605 mailed Jun. 1, 2010, 3 pages.
Office Action issued for CN 200880002425.9 on Mar. 2, 2011, 10 pages with English translation.
Office Action issued for EP 06768437.3 (EPO Form1224) issued on Oct. 28, 2010, 47 pages.
Office Action issued for European Search Report for European Application No. 06782407 on Sep. 29, 2011, 6 pages.
Office Action issued for Japanese Application No. 2007-529565 issued on Dec. 13, 2011, 7 pages with English full translation.
Office Action issued for JP Appl. No. 2007-529565 issued on May 8, 2012, 6 pages with English translation.
Office Action issued in MX App. Ser. No. MX/a/2012/002011, dated Jul. 17, 2013, 6 pages (with English translation).
Office Action issued Jan. 7, 2011, in U.S. Appl. No. 12/092,539, 12 pages.
Office Action, U.S. Appl. No. 11/347,749 mailed Feb. 9, 2009, 6 pages.
Office Communication dated Sep. 13, 2004 for U.S. Appl. No. 10/420,466, 7 pages.
Office Letter Confirmation of Amendment After Allowance dated Jan. 11, 2011 for CA App. Ser. No. 2426461, 1 pages.
Office Letter re Notice of Allowance dated May 25, 2012 for ZA App. Ser. No. 201108697, 3 pages.
Official Letter and Notice of Allowance for AU App. Ser. No. 2008325608, dated Feb. 27, 2013, 7 pages.
Official Letter and Notice of Allowance for AU App. Ser. No. 2008211952, dated Jul. 10, 2012, 10 pages.
Official Letter re Grant of Request for Correction of Specification for SG App. Ser. No. 201108602-2, dated Aug. 8, 2012, 2 pages.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," *Ann Oncol.*, 18(2):317-323 (2007).
Okayama et al., "Activation of Eosinophils with Cytokines Produced by Lung Mast Cells," *Int Arch Allergy Immunol.*, 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," *Eur. J. Immunol.*, 28:708-715 (1998).
Okura et al., "Effects of monoclonal anti-c-kit antibody (ACK2) on melanocytes in newborn mice," *J. Invest. Dermatol.*, 105(3):322-328 (1995).
Olaso et al., "DDR2 receptor promotes MMP-2-mediated proliferation and invasion by hepatic stellate cells," *J. Clin. Invest.*, 108(9):1369-1378 (2001).
Ozols et al., "Phase III trial of carboplatin and paclitaxel compared with cisplatin and paclitaxel in patients with optimally resected stage III ovarian cancer: a Gynecologic Oncology Group study," *J. Clin. Oncol.*, 21(17):3194-3200 (2003).
Pakistani Office Action for App. Ser. No. 94/2011, issued on May 9, 2012, 2 pages.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
Partial European Search Report for App. Ser. No. 01976786.2, dated Apr. 6, 2004, 5 pages.
Paterson et al., "Preclinical studies of fibroblast growth factor receptor 3 as a therapeutic target in multiple myeloma," *British Journal of Haematology*, 124:595-603 (2004).
Paulus, "Preparation and Biomedical Applications of Bispecific Antibodies", Behring Inst. Mitt. 78: 118-132 (1985).
Paz et al., "Development of angiogenesis inhibitors to vascular endothelial growth factor receptor 2. Current status and future perspective," *Frontiers in Bioscience*, 10:1415-1439 (May 1, 2005).
Pearson, "Rapid and Sensitive Sequence Comparison with FASTP and FASTA", Methods in Enzymology 183 :63-98 (1990).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood.,103, 3474-3479, 2004.
Polverino et al, "AMG 706, an Oral, Multikinase Inhibitor that Selectively Targets Vascular Endothelial Growth Factor, Platelet—Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed Aug. 10, 2011, 24 pages.
Preliminary Amendment and Response to Restriction Requirement in U.S. Appl. No. 13/083,338, filed Apr. 30, 2012, 16 pages.
Preliminary Amendment dated Apr. 26, 2013 for U.S. Appl. No. 13/870,507, 10 pages.
Preliminary Amendment filed on Apr. 18, 2003 for U.S. Appl. No. 10/420,466, 376 pages.
Preliminary Amendment filed on Dec. 2, 2005 for U.S. Appl. No. 10/420,466, 36 pages.

(56) References Cited

OTHER PUBLICATIONS

Preliminary Amendment filed on Feb. 3, 2006 for U.S. Appl. No. 11/293,785, 33 pages.
Preliminary Amendment filed on May 23, 2003 for KR App. Ser. No. 10-2003-7005506, 42 pages (with English translation).
Preliminary Amendment filed on Oct. 27, 2003 for U.S. Appl. No. 10/420,517, 41 pages.
Preliminary Amendment for U.S. Appl. No. 13/624,278, filed Sep. 21, 2012, 7 pages.
Pritzker, "Cancer Biomarkers: Easier Said Than Done," Clinical Chemistry, 48(8):1147-1150 (2002).
Reasons for Reexamination dated Sep. 11, 2012 for CN App. Ser. No. 200680020317.5, 7 pages (with English translation).
Reexamination filed on May 25, 2004 for TW App. Ser. No. 90125928, 59 pages (with English translation).
Reexamination filed on Nov. 25, 2004 for TW App. Ser. No. 90125928, 59 pages (with English translation).
Registered dated Feb. 24, 2009 for PH App. Ser. No. 1-2003-500266, 3 pages.
Rejection dated Apr. 26, 2004 for TW App. Ser. No. 90125928, 10 pages (with English translation).
Reply to communication from the Examining Division for EP App. Ser. 06023078.6, dated Feb. 4, 2008, 97 pages.
Reply to communication from the Examining Division for EP App. Ser. 06023078.6, dated Sep. 11, 2007, 10 pages.
Reply to communication from the Examining Division for EP App. Ser. No. 01976786.2, dated Jan. 25, 2006, 36 pages.
Reply to communication from the Examining Division for EP App. Ser. No. 01976786.2, dated Jul. 19, 2006, 124 pages.
Reply to communication from the Examining Division for EP App. Ser. No. 04025700.8, dated Feb. 15, 2007, 2 pages.
Reply to communication from the Examining Division for EP App. Ser. No. 04025700.8, dated Jan. 26, 2007, 232 pages.
Reply to communication from the Examining Division for EP App. Ser. No. 04025700.8, dated Sep. 12, 2006, 21 pages.
Reply to Examination Report dated Feb. 8, 2013 for EP App. Ser. No. 07743994.1, 4 pages.
Reply to official communication for EP App. Ser. No. 05783232.1, dated Apr. 30, 2008, 13 pages.
Reply to the invitation to remedy deficiencies for EP App. Ser. No. 06023078.6, dated Jan. 11, 2007, 3 pages.
Request for amendment of the text intended for grant and translation of claims for EP App. Ser. No. 04025700.8, dated Feb. 1, 2008, 41 pages.
Request for amendment of the text intended for grant and translation of claims for EP App. Ser. No. 06023078.6, dated Nov. 5, 2008, 19 pages.
Request for Continued Examination (RCE) transmittal for U.S. Appl. No. 12/864,817, filed Dec. 22, 2011, 1 page.
Request for correction of errors in filed documents for EP App. Ser. No. 06023078.6, dated Feb. 13, 2007, 4 pages.
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Request for Substantive Examination for ID App. Ser. No. W-00201201031, filed Jun. 3, 2013, 6 pages (with English translation).
Request for Substantive Examination for UA App. Ser. No. a201203132, filed Apr. 15, 2013, 16 pages (with English translation).
Request for Voluntary Amendments filed May 10, 2012, in Ukraine Patent Application No. A 2012 03132, 11 pages with English Abstract.
Request to Amend Complete Specification dated Feb. 15, 2013 for AU App. Ser. No. 2008325608, 23 pages.
Request to Amend Complete Specification dated May 9, 2013 for AU App. Ser. No. 2009210098, 22 pages.
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response and Amendment for CA App. Ser. No. 2652442, dated Sep. 5, 2013, 17 pages.
Response filed in IN App. Ser. No. 1571/CHENP/2007, dated Oct. 30, 2013, 9 pages.
Response filed on Apr. 11, 2006 for CN App. Ser. No. 01819710.8, 4 pages (with English translation).
Response filed on Apr. 17, 2007 for PH App. Ser. No. 1-2003-500266, 1 page.
Response filed on Apr. 27, 2006 for AU App. Ser. No. 2001295986, 22 pages.
Response filed on Apr. 30, 2008 for PH App. Ser. No. 1-2003-500266, 1 page.
Response filed on Aug. 13, 2009 for CA App. Ser. No. 2426461, 4 pages.
Response filed on Aug. 14, 2006 for PH App. Ser. No. 1-2003-500266, 1 page.
Response filed on Aug. 18, 2008 for NO App. Ser. No. 20031731, 2 pages (with English translation).
Response filed on Aug. 21, 2006 for MX App. Ser. No. PA/a/2003/003362, 5 pages (with English translation).
Response filed on Aug. 26, 2004 for NZ App. Ser. No. 525324, 3 pages.
Response filed on Aug. 5, 2003 for PH App. Ser. No. 1-2003-500266, 1 page.
Response filed on Dec. 11, 2007 for TW App. Ser. No. 90125928, 54 pages (with English translation).
Response filed on Dec. 15, 2005 for MX App. Ser. No. PA/a/2003/003362, 9 page (with English translation).
Response filed on Dec. 4, 2007 for IL App. Ser. No. 155447, 35 pages (with English translation).
Response filed on Feb. 23, 2009 for CA App. Ser. No. 2426461, 31 pages.
Response filed on Feb. 26, 2008 for U.S. Appl. No. 11/293,785, 16 pages.
Response filed on Jan. 11, 2010 for CN App. Ser. No. 200580026468.7, 4 pages (with English translation).
Response filed on Jan. 21, 2005 for NZ App. Ser. No. 525324, 2 pages.
Response filed on Jan. 26, 2010 for CN App. Ser. No. 200710007097.9, 3 pages (with English translation).
Response filed on Jan. 26, 2011 for IL App. Ser. No. 181697, 5 pages (with English translation).
Response filed on Jul. 1, 2005 for U.S. Appl. No. 10/420,466, 14 pages.
Response filed on Jul. 2, 2009 for CN App. Ser. No. 200710007097.9, 4 pages (with English translation).
Response filed on Jul. 26, 2006 for AU App. Ser. No. 2001295986, 11 pages.
Response filed on Jul. 31, 2007 for PH App. Ser. No. 1-2003-500266, 1 page.
Response filed on Jun. 22, 2010 for CN App. Ser. No. 200710007097.9, 3 pages (with English translation).
Response filed on Mar. 17, 2005 for RU App. Ser. No. 2003114740, 75 pages (with English translation).
Response filed on May 13, 2009 for IL App. Ser. No. 189677, 125 pages (with English translation).
Response filed on May 16, 2008 for CA App. Ser. No. 2426461, 79 pages.
Response filed on May 20, 2010 for CA App. Ser. No. 2426461, 23 pages.
Response filed on May 7, 2008 for NO App. Ser. No. 20031731, 2 pages (with English translation).
Response filed on May 8, 2008 for AU App. Ser. No. 2006236039, 2 pages.
Response filed on Nov. 19, 2009 for CN App. Ser. No. 200710007097.9, 9 pages (with English translation).
Response filed on Nov. 30, 2004 for RU App. Ser. No. 2003114740, 90 pages (with English translation).
Response filed on Oct. 13, 2008 for NO App. Ser. No. 20031731, 400 pages (with English translation).

(56) References Cited

OTHER PUBLICATIONS

Response filed on Oct. 15, 2007 for PH App. Ser. No. 1-2003-500266, 1 page.
Response filed on Oct. 8, 2004 for U.S. Appl. No. 10/420,466, 19 pages.
Response filed on Oct. 9, 2006 for CN App. Ser. No. 01819710.8, 2 pages (with English translation).
Response filed on Sep. 10, 2007 for NO App. Ser. No. 20031731, 60 pages (with English translation).
Response filed on Sep. 13, 2005 for CN App. Ser. No. 01819710.8, 7 pages (with English translation).
Response filed on Sep. 15, 2003 for PH App. Ser. No. 1-2003-500266, 1 page.
Response filed on Sep. 21, 2011 for CA App. Ser. No. 2579810, 16 pages.
Response filed on Sep. 23, 2009 for CN Patent Application No. 200580026468.7, 4 pages with English translation.
Response filed on Sep. 8, 2003 for PH App. Ser. No. 1-2003-500266, 1 page.
Response to AU OA for AU 2008211952 filed on Jun. 28, 2012, 36 pages.
Response to Australian Office Action filed on Apr. 29, 2010 for corresponding AU Application No. 2006285673, 11 pages.
Response to Australian Office Action filed on Jul. 28, 2010 for corresponding AU Application No. 2006285673, 6 pages.
Response to Australian Office Action filed on Oct. 16, 2009 for corresponding AU Application No. 2006285673, 14 pages.
Response to Canadian Office Action filed Feb. 13, 2012, in Canadian Application No. 2,620,594, 8 pages.
Response to Canadian Office Action filed on Apr. 12, 2011 for corresponding CA Application No. 2,620,594, 4 pages.
Response to Canadian Office Action filed on Jun. 21, 2010 for corresponding CA Application No. 2,620,594, 18 pages.
Response to Chinese Office Action filed on Mar. 5, 2010 for corresponding CN Application No. 200680036592.6, 11 pages with English translation.
Response to Chinese Office Action filed on Jul. 11, 2012 for Chinese Patent Application No. 200680036592.6, 17 pages with English translation.
Response to Chinese Office Action for CN 200680020317.5 dated Sep. 11, 2012, 7 pages with English translation.
Response to CN OA for CN200880003336.6 filed on May 3, 2012, 15 pages.
Response to EP OA for EP 07806561.2 filed on Apr. 18, 2012, 8 pages.
Response to IL OA for IL 195282 filed on May 28, 2012, 5 pages.
Response to Indian Office Action issued Feb. 2, 2012, dated Jun. 22, 2012, for Application No. 1908/DELNP/2008, 27 pages.
Response to Israeli Office Action filed on Sep. 7, 2010 for the corresponding Israeli Application No. 189589, 9 pages.
Response to Israeli Office Action, filed Jul. 24, 2012 for corresponding Israeli Patent Application No. 189589, 7 pages.
Response to Japanese Office Action dated Jul. 17, 2012 for Japanese Application No. 2007-533350, 12 pages with English translation.
Response to Japanese Office Action filed on Jan. 9, 2013 for corresponding Japanese Application JP-2007-533350, 6 pages.
Response to Korean Office Action filed on Feb. 24, 2010 for corresponding KR Application No. 10-2008-7005195, 31 pages with English translation.
Response to Korean Office Action filed on Jul. 29, 2010 for corresponding KR Application No. 10-2008-7005195, 26 pages with English translation.
Response to Notice of Allowability filed on Dec. 13, 2007 for PH App. Ser. No. 1-2003-500266, 1 page.
Response to Notice Prior to Examination filed in IL App. Ser. No. 217197, filed Jul. 31, 2013, 9 pages (with English translation).
Response to Notice Prior to Examination filed on Apr. 22, 2009 for IL App. Ser. No. 181697, 11 pages (with English translation).
Response to Notice Prior to Examination filed on Jan. 11, 2009 for IL App. Ser. No. 189677, 7 pages (with English translation).
Response to OA for EP 10015141 filed on Mar. 5, 2012, 47 pages.
Response to Office Action dated Feb. 7, 2013 for CN App. Ser. No. 201080030508.6, 17 pages (with English translation).
Response to Office Action dated Jul. 5, 2012 for CN App. Ser. No. 200880115011.7, 24 pages (with English translation).
Response to Office Action dated Nov. 30, 2012 for CN App. Ser. No. 200780017371.9, 4 pages (with English translation).
Response to Office Action directed at Australian Appl. No. 2006309551 filed on Mar. 28, 2012, 27 pages.
Response to Office Action filed on Jan. 25, 2013 for CA App. Ser. No. 2627598, 9 pages.
Response to Office Action filed on Jul. 11, 2012 for CN App. Ser. No. 200880003336.6 (with English translation), 10 pages.
Response to Office Action filed on May 29, 2012 for RU App. Ser. No. 2012103471 (with English translation), 7 pages.
Response to Office Action for EP 08704376.6 dated Jan. 2, 2013, 22 pages.
Response to Office Action for IL 199907 filed on Oct. 11, 2010, 4 pages with English translation.
Response to Office Action for Israeli App. Ser. No. 205512, filed on Mar. 11, 2012 (with English translation), 12 pages.
Response to Office Action for Israeli App. Ser. No. 207089, filed on Mar. 11, 2012, with English translation, 13 pages.
Response to Office Action for MX App. Ser. No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005, 14 pages.
Response to Office Action under 37 C.F.R. §1.111 for U.S. Appl. No. 12/523,495, filed Dec. 7, 2011, 13 pages.
Response to Office Action under 37 C.F.R. §1.111 for U.S. Appl. No. 13/083,338, filed Sep. 6, 2012, 8 pages.
Response to Office Action under 37 C.F.R. §1.111 for U.S. Appl. No. 13/083,338, filed on Apr. 8, 2011, 6 pages.
Response to Office Action under 37 C.F.R. §1.111 for Information Disclosure Statement for U.S. Appl. No. 11/997,719, filed Jul. 3, 2013, 26 pages.
Response to Restriction Requirement for U.S. Appl. No. 11/997,543, filed Mar. 22, 2011, 4 pages.
Response to Restriction Requirement for U.S. Appl. No. 12/301,353, filed Nov. 23, 2010, 4 pages.
Response to Restriction Requirement for U.S. Appl. No. 12/524,754, filed Dec. 1, 2011, 2 pages.
Response to Restriction Requirement in U.S. Appl. No. 13/238,085, dated Oct. 4, 2013, 3 pages.
Response to the European Search Report for European Application No. 06782407 filed on Nov. 8, 2010, 105 pages.
Response to the Office Action for European Application No. 06782407 filed on Jan. 23, 2012, 17 pages.
Response to the Office Action issued for Japanese Application No. 2007-529565 filed on Feb. 3, 2012, 44 pages with English full translation.
Restriction Requirement for U.S. Appl. No. 12/092,539, dated Oct. 29, 2010, 8 pages.
Restriction Requirement for U.S. Appl. No. 12/301,353, dated Oct. 29, 2010, 11 pages.
Restriction Requirement for U.S. Appl. No. 12/439,339, dated Jul. 29, 2011, 10 pages.
Restriction Requirement for U.S. Appl. No. 12/524,754, dated Nov. 3, 2011, 11 pages.
Roberts et al., "Antiangiogenic and Antitumor Activity of a Selective PDGFR Tyrosine Kinase Inhibitor, CP-673,451", Cancer Research., 65, 957-966, 2005.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Modelsl", Cancer Research., 63, 5978-5991, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.

(56) References Cited

OTHER PUBLICATIONS

Russian Decision of Grant directed at Appl. No. 2008149948115(065561) received on Nov. 9, 2011, 16 pages with English translation.
Russian Office Action dated Apr. 11, 2012 for App. Ser. No. 2012103471, 6 pages (with English translation).
Russian Office Action dated Jan. 19, 2005 for App. Ser. No. 2003114740 (with English translation), 3 pages.
Russian Office Action dated Jun. 29, 2004 for App. Ser. No. 2003114740 (with English translation), 16 pages.
Russian Office Action directed at Appl. No. 2008149948115(065561) issued on May 24, 2011, 8 pages with English translation.
Russian Response to Office Action directed at Appl. No. 2008149948115(065561) filed on Jul. 27, 2011, 14 pages with English translation.
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Salmon et al., "Anti-angiogenic treatment of gastrointestinal malignancies," *Cancer Invest.*, 23(8):712-726 (2005).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Sandler et al., "Phase III trial of gemcitabine plus cisplatin versus cisplatin alone in patients with locally advanced or metastatic non-small-cell lung cancer," *J Clin. Oncol.*, 18(1):122-130 (2000).
Sanger et al., "DNA sequencing with chain-terminating inhibitors", Proc. NatI. Acad. Sci. Usa 74: 5463 (1977).
Santoro et al., "Drug insight: Small-molecule inhibitors of protein kinases in the treatment of thyroid cancer," *Nat. Clin. Pract. Endocrinol. Metab.*, 2(1):42-52 (2006).
Santoro et al., "Minireview: RET: normal and abnormal functions," *Endocrinology*, 145:5448-5451 (2004).
Santoro et al., "Molecular Mechanisms of RET Activation in Human Cancer," *Ann. N.Y. Academy of Sciences*, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," *Oncogene*, 21:3314-3333 (2002).
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Second Preliminary Amendment and Response to Restriction Requirement for U.S. Appl. No. 12/092,539, filed Nov. 22, 2010, 5 pages.
Sekido et al., "Preferential Expression of c-kit Protooncogene Transcripts in Small Cell Lung Cancer," Cancer Res., 51:2416-2418 (1991).
Shiang et al., "Mutations in the transmembrane domain of FGFR3 cause the most common genetic form of dwarfism, achondroplasia," *Cell.*, 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors," *Bioorganic and Medicinal Chemistry Letters*, 14(4):875-879 (2004).
Shirai, et al., ""Role of llow-substituted hydroxypropylcellulose in dissociation and bioavalability of novel fine granule system for masking bitter taste," Biol. Pharm. Bull, 17(3): 427-431 (1994)."
Siegel et al., "Sorafenib: Where Do We Go from Here?," *Hepatology*, 52:360-369 (2010).

Siemeister et al., "ZK304709, the oral Multitarget Tumor Growth Inhibitor™, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).
Spacey et al., "Indolocarbazoles, Potent and Selective Inhibitors of Platelet-Derived Growth Factor Receptor Autophosphorylation," *Biochemical Pharmacology*, 55:261-271 (1998).
St. Bernard et al., "Fibroblast Growth Factor Receptors as Molecular Targets in Thyroid Carcinoma," Endocrinology, Mar. 2005, 146(3):1145-1153.
Strohmeyer et al., "Expression of the hst-1 and c-kit Protoonocogenes in Human Testicular Germ Cell Tumors," *Cancer Res.*, 51:1811-1816 (1991).
Submission Document(s) Before the Patent Office for IL App. Ser. No. 200090, dated Dec. 23, 2012, 16 pages, with English translation.
Submission Document Before the Patent Office dated Apr. 22, 2013 for IL App. Ser. No. 207089, 7 pages (with English translation).
Submission Document Before the Patent Office dated Mar. 14, 2013 for IL App. Ser. No. 205512, 12 pages (with English translation).
Submission Document Before the Patent Office for CL App. Ser. No. 2012-00412, dated Aug. 31, 2012, 6 pages (with English translation).
Submission Document Before the Patent Office for EP App. Ser. No. 03791389.4, dated Dec. 20, 2012, 4 pages.
Submission Document Before the Patent Office for EP App. Ser. No. 08846814.5, dated Jan. 3, 2013, 102 pages.
Submission Document Before the Patent Office re Observation dated Feb. 16, 2013 for CN App. Ser. No. 200980103218.7, 6 pages (with English translation).
Submission Document Before the Patent Office re RCE in U.S. Appl. No. 13/205,328, dated Sep. 10, 2013, 1 page.
Submission Document re Petition on Oct. 2, 2013 in CL App. Ser. No. 2012-00412, 22 pages (with English translation).
Submission Document re RCE and Information Disclosure Statement on Sep. 19, 2013 in U.S. Appl. No. 12/741,682, 19 pages.
Submission Document re RCE and Information Disclosure Statement on Oct. 18, 2013, in U.S. Appl. No. 12/524,754, 17 pages.
Submission Documents Before the Patent Office for CN App. Ser. No. 201080030508.6, dated May 27, 2013, 7 pages (with English translation).
Submission Documents Before the Patent Office for KR App. Ser. No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents re New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission of Amendments and Complete Specification dated Apr. 10, 2013 for in App. Ser. No. 1571/CHENP/2007, 15 pages.
Submission of Document Before the Patent Office re Request for Voluntary Amendments dated Jan. 30, 2013 for NZ App. Ser. No. 598291, 8 pages.
Submission of Document re Claims filed in Response to Second Office Action for CN App. Ser. No. 200880115011.7, filed on Nov. 20, 2012, 16 pages.
Submission of Document re Request for Examination in CO App. Ser. No. 12-022608, submitted on Jun. 12, 2012, 6 pages.
Submission of Documents before the Patent Office for CN App. Ser. No. 200980103218.7, dated Mar. 13, 2013, 6 pages (with English translation).
Submission of Documents before the Patent Office for CN App. Ser. No. 200880115011.7, dated Apr. 11, 2013, 10 pages (with English translation).

(56) References Cited

OTHER PUBLICATIONS

Submission of Documents Before the Patent Office for IL App. Ser. No. 175363, dated Feb. 27, 2013, 22 pages.
Submission of Documents re Amendment in UA App. Ser. No. a2012 03132, submitted on May 22, 2012, 11 pages (with English translation).
Submission of Documents re Claim 3 and Figure 3 for KR App. Ser. No. 10-2009-7005657, filed on Jul. 13, 2012, 5 pages.
Submission of Reference Materials in KR App. Ser. No. 10-2008-7013685, filed Jul. 5, 2013, 43 pages, (with English translation).
Sun et al., "Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5[5-Fluoro-2-oxo-1,2-dihydroindol-(3Z)-ylidenemethyl]-2,4-dimethy1-1H-pyrrole-3carboxylic acid . . . Tyrosine Kinase", Journal of Medicinal Chemistry., 46:1116-1119.
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplementary European Search Report for App. Ser. No. 01976786.2, dated Jul. 6, 2004, 6 pages.
Supplementary European Search Report issued Jul. 5, 2012, in European Patent Application No. 08846814.5, 1 page.
Suzuki et al., "MP-412, a dual EGFR/HER2 tyrosine kinase inhibitor: 1. In vivo kinase inhibition profiled," Am. Assoc. Cancer Research, A3405, 2005, 2 pages.
Taguchi et al., "A novel orally active inhibitor of VEGF receptor tyrosine kinases KRN951: Anti-angiogenic and anti-tumor activity against human solid tumors," Proc Am Assoc Cancer Res., 45:1070-1071, Abstract 2575, 2004.
Takahashi et al., "A case of inoperable scirrhous gastric cancer that responded remarkably to a combination of TS-1+paclitaxel and showed complete loss of ascites," Japanese Journal of Cancer and Chemotherapy, 31(7):1093-1095 (2004).
Takeda et al., "AZD2171 shows potent anti-tumor activity against gastric cancer expressing variant K-SAM/FGFR2," Abstract #3785, *Proceeding of the American Association for Cancer Research*, 47:890 (2006).
Tan et al., "Randomized study of vinorelbine—gemcitabine versus vinorelbine—carboplatin in patients with advanced non-small cell lung cancer," *Lung Cancer*, 49(2):233-240 (2005).
Taniguchi et al., "Effect of c-kit Mutation on Prognosis of Gastrointestinal Stromal Tumors," *Cancer Res.*, 59:4297-4300 (1999).
The Pharmacology of Monoclonal Antibody, vol. 113, Chapter 11, Rosenburg and Moore ed., Springer Verlag (1994) pp. 269-315.
Third Office Action dated Feb. 25, 2013 for CN App. Ser. No. 200880115011.7, 6 pages (with English translation).
Thomas et al., "The Eosinophil and its Role in Asthma," *Gen. Pharmac.*, 27(4)593-597 (1996).
Thyroid Cancers, Endocrine and Metabolic Disorders, http://www.merkmanuals.com/professional/print/sec12/ch152/ch152j.html Mar. 16, 2011, 4 pages.
Tian et al., "Activating c-kit Gene Mutations in Human Germ Cell Tumors," American Journal of Pathology, 154(6):1643-1647 (1999).
Tohyama et al., "P-3111, Preclinical effect of lenvatinib on human thyroid cancer targeting angiogenesis and receptor tyrosine kinase signaling," The 71$^{st}$ Annual Meeting of the Japanese Cancer Association, Sep. 19-21, 2012, p. 502.
Tonary et al., "Lack of expression of c-KIT in ovarian cancers is associated with poor prognosis," *Int. J. Cancer*, 89:242-250 (2000).
Tong et al., "Vascular normalization by vascular endothelial growth factor receptor 2 blockade induces a pressure gradient across the vasculature and improves drug penetration in tumors," *Cancer Res.*, 64:3731-3736 (2004).
Toshiyuki et al., "Thermal recording materials with improved background stability," Database CA (Online) Chemical Abstracts Service, Columbus, OH, US (Feb. 20, 1996) (XP002443195), 1 page.

Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011, 15 pages.
Traxler et al., "AEE788; A dual family epidermal growth factor receptor/ErbB2 and vascular endothelial growth factor receptor tyrosine kinase inhibitor with antitumor and antiangiogenic activity," *Cancer Res.*, 64:4931-4941 (2004).
Trudel et al., "CHIR-258, a novel, multitargeted tyrosine kinase inhibitor for the potential treatment of t(4;14) multiple myeloma," *Blood*, 105:2941-2948 (2005).
Trudel et al., "Inhibition of fibroblast growth factor receptor 3 induces differentiation and apoptosis in t(4;14) myeloma," *Blood*, 103:3521-3528 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Turner et al., "Fibroblast growth factor signaling: from development to cancer," *Nature Reviews*, Cancer, 10:116-129 (2010).
U.S. Notice of Allowance for U.S. Appl. No. 12/244,227, dated Oct. 22, 2010, 32 pages.
U.S. Office Action for U.S. Appl. No. 10/420,466, issued on Apr. 13, 2005, 16 pages.
U.S. Office Action for U.S. Appl. No. 10/797,903, issued on Apr. 1, 2010, 11 pages.
U.S. Office Action for U.S. Appl. No. 10/797,903, issued on Sep. 1, 2010, 7 pages.
U.S. Office Action for U.S. Appl. No. 11/293,785, issued on Sep. 4, 2007, 18 pages.
U.S. Office Action for U.S. Appl. No. 11/662,425, issued on May 3, 2010, 16 pages.
U.S. Office Action for U.S. Appl. No. 11/662,425, issued on Sep. 28, 2010, 35 pages.
U.S. Office Action for U.S. Appl. No. 11/997,543, issued on Feb. 23, 2011, 9 pages.
U.S. Office Action for U.S. Appl. No. 11/997,543, issued on May 19, 2011, 38 pages.
U.S. Office Action for U.S. Appl. No. 11/997,543, issued on Nov. 9, 2011, 12 pages.
U.S. Office Action for U.S. Appl. No. 11/997,719, issued on Apr. 6, 2011, 6 pages.
U.S. Office Action for U.S. Appl. No. 11/997,719, issued on Sep. 3, 2010, 10 pages.
U.S. Office Action for U.S. Appl. No. 12/092,539, issued on Jun. 28, 2011, 3 pages.
U.S. Office Action for U.S. Appl. No. 12/092,539, issued on May 9, 2011, 10 pages.
U.S. Office Action for U.S. Appl. No. 12/094,492, issued on Mar. 24, 2011, 16 pages.
U.S. Office Action for U.S. Appl. No. 12/301,353, issued on Jan. 24, 2011, 10 pages.
U.S. Office Action for U.S. Appl. No. 12/400,562, issued on Mar. 31, 2010, 11 pages.
U.S. Office Action for U.S. Appl. No. 12/439,339, issued on Mar. 30, 2012, 6 pages.
U.S. Office Action for U.S. Appl. No. 12/439,339, issued on Nov. 14, 2011, 44 pages.
U.S. Office Action for U.S. Appl. No. 12/523,495, issued on Dec. 27, 2011, 11 pages.
U.S. Office Action for U.S. Appl. No. 12/523,495, issued on Sep. 27, 2011, 37 pages.
U.S. Office Action for U.S. Appl. No. 12/524,754, issued on Dec. 19, 2011, 53 pages.
U.S. Office Action for U.S. Appl. No. 12/741,682, issued on Apr. 30, 2012, 50 pages.
U.S. Office Action for U.S. Appl. No. 12/864,817, issued on Dec. 16, 2011, 4 pages.
U.S. Office Action for U.S. Appl. No. 12/864,817, issued on May 19, 2011, 11 pages.
U.S. Office Action for U.S. Appl. No. 12/864,817, issued on Nov. 3, 2011, 11 pages.

(56) References Cited

OTHER PUBLICATIONS

U.S. Office Action for U.S. Appl. No. 13/083,338, issued on Apr. 12, 2012, 8 pages.
U.S. Office Action for U.S. Appl. No. 13/083,338, issued on Jun. 8, 2012, 55 pages.
U.S. Office Action for U.S. Appl. No. 13/083,338, issued on Nov. 23, 2012, 38 pages.
U.S. Office Action for U.S. Appl. No. 13/205,328, issued on Jan. 12, 2012, 37 pages.
U.S. Office Action for U.S. Appl. No. 13/205,328, issued on May 1, 2012, 21 pages.
U.S. Office Action for U.S. Appl. No. 13/322,961, issued on Sep. 25, 2012, 62 pages.
Ueda et al., "VGA1155, a Novel Binding Antagonist of VEGF, Inhibits Angiogenesis in Vitro and in Vivo", Anticancer Research., 24, 3009-3017, 2004.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
US Office Action for U.S. Appl. No. 11/997,543, dated Sep. 30, 2013, 88 pages.
US Response to Notice of Non-Compliant Amendment dated Jan. 13, 2005 for U.S. Appl. No. 10/420,466, 17 pages.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
van Oers et al., "A simple and fast method for the simultaneous detection of nine fibroblast growth factor receptor 3 mutations in bladder cancer and voided urine," Clin. Cancer Res., 11:7743-7748 (2005).
Vippagunta et al., "Crystalline solids," *Advanced Drug Delivery Reviews*, 48:3-26 (2001).
Vogel et al., "Sensing extracellular matrix: an update on discoidin domain receptor function," *Cell Signaling*, 18:1108-1116 (2006).
Voluntary Amendment filed in CA App. Ser. No. 2704000, filed Aug. 6, 2013, 6 pages.
Voluntary Amendment filed on Aug. 11, 2010 for CN App. Ser. No. 200710007097.9, 12 pages (with English translation).
Voluntary Amendment filed on Aug. 19, 2010 for CA App. Ser. No. 2426461, 2 pages.
Voluntary Amendment filed on Aug. 30, 2006 for AU App. Ser. No. 2006203099, 16 pages.
Voluntary Amendment filed on Feb. 16, 2012 for BR Patent App. No. BR112012003592-4, 18 pages (with partial English translation).
Voluntary Amendment filed on Feb. 27, 2007 for AU App. Ser. No. 2006236039, 10 pages.
Voluntary Amendment filed on Feb. 9, 2010 for AU App. Ser. No. 2005283422, 12 pages.
Voluntary Amendment filed on Jul. 6, 2010 for AU App. Ser. No. 2005283422, 21 pages.
Voluntary Amendment filed on Sep. 10, 2010 for HU App. Ser. No. P0302603, 36 pages (with English translation).
Voluntary Amendment for Australian App. Ser. No. 2010285740, filed on Nov. 21, 2011, 3 pages.
Voluntary Amendment for Chinese counterpart of App. No. PCT/JP2010/063804, filed on Jan. 5, 2012, 8 pages (with English translation).
Voluntary Amendment for counterpart Canadian patent application, filed on Feb. 16, 2012, 3 pages.
Voluntary Amendment for Russian App. Ser. No. 2012103471, filed on Feb. 1, 2012, 3 pages (with English translation).
Voluntary Amendment for Thailand App. Ser. No. 1201000221, filed on Feb. 17, 2012, 8 pages.
Voluntary Brief Amendments for Venezuelan App. Ser. No. 2011-000193, filed on Dec. 21, 2011, 8 pages (with English translation).
Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," *Japanese Journal of Cancer and Chemotherapy*, 21(14):2398-2406 (1994) (English abstract).
Wang et al., "A Convenient Set of Bidentate Pyridine Ligands for Combinatorial Synthesis," *Tetrahedron Lett.*, 40:4779-1478 (1999).
Wang et al., "Phase II study of gemcitabine and carboplatin in patients with advanced non-small-cell lung cancer," *Cancer Chemother Pharmacol.*, 60(4):601-607 (2007).
Wang et al., "The Expression of the Proto-Oncogene C-Kit in the Blast Cells of Acute Myeloblastic Leukemia," *Leukemia*, 3(10):699-702 (1989).
Wang, "Everolimus in renal cell carcinoma," Drugs of Today, Aug. 2010, 46(8), abstract, 1 page.
Waterman, M., "Computer Analysis of Nucleic Acid Sequences", Methods in Enzymology, 164:765-793 (1988).
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wedge et al., "AZD2171: a highly potent, orally bioavailable, vascular endothelial growth factor receptor-2 tyrosine kinase inhibitor for the treatment of cancer," *Cancer Res.*, 65(10):4389-4400 (2005).
Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 24-28, 2001, New Orleans, LA, USA, abstract 3126, 2 pages.
Wells et al., "Targeting the RET Pathway in Thyroid Cancer," *Clin. Cancer Res.*, 15:7119-7123 (2009).
Werner et al., "Gastric adenocarcinoma: pathomorphology and molecular pathology," J. Cancer Res. Clin. Oncology, 127:207-216 (2001) (English abstract).
Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur, W.J. and Lipman, DJ., "Rapid similarity searches of nucleic acid and protein data banks", Natl. Acad. Sci, U.S.A. 80:726-730 (1983).
Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Wisniewski et al., "Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research, 64, 6652-6659. 2004.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Wozniak et al., "Randomized trial comparing cisplatin with cisplatin plus vinorelbine in the treatment of advanced non-small-cell lung cancer: a Southwest Oncology Group study," *J. Clin. Oncol.*, 16(7):2459-2465 (1998).
Written Amendment filed on Jun. 16, 2009 for JP App. Ser. No. 2009-123432, 12 pages (with English translation).
Written Amendment filed on Sep. 21, 2011 for JP App. Ser. No. 2011-527665, 2 pages (with English translation).
Written Statement filed on Jun. 16, 2009 for JP App. Ser. No. 2009-123432, 32 pages (with English translation).
Written Statement filed on Sep. 21, 2011 for JP App. Ser. No. 2011-527665, 2 pages (with English translation).
Wu et al., "A fully human monoclonal antibody against VEGFR-1 inhibits growth of human breast cancers," Proceedings of the American Association for Cancer Research, 45, 694, (Abstract 3005), 2004, 3 pages.

(56) References Cited

OTHER PUBLICATIONS

Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.

Yamada et al., "New technique for staining," *Monthly Medical Technology Supplementary Volume* (Apr. 1999) (with English translation).

Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, *AACR*, Toronto, Canada (Apr. 5-9, 2003).

Yamamoto et al., "E7080 a novel multitargeted tyrosine kinase inhibitor, has direct anti-tumor activity via inhibition of KIT signaling in small cell lung cancer," Abstract #4636, *AACR*, Orlando, FL, (Mar. 27-31, 2004).

Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, *97th Annual Meeting AACR*, Washington, DC. (Apr. 1-5, 2006).

Yamamoto et al., "E7080, an oral multi-targeted tyrosine kinase inhibitor, has direct anti-tumor efficacy via inhibition of KIT signaling in small cell lung cancer," *Proceedings of the American Association for Cancer Research*,45:1070-1071 (Mar. 2004).

Yanagihara et al., "Development and biological analysis of peritoneal metastasis mouse models for human scirrhous stomach cancer," *Cancer Sci.*, 96(6):323-332 (2005).

Yigitbasi et al., "Tumor Cell and Endothelial Cell Therapy of Oral Cancer by Dual Tyrosine Kinase Receptor Blockade", Cancer Research, 64, 7977-7984, 2004.

Yu, "Amorphous Pharmaceutical Solids:Preparation Characterization and Stabilization," *Advanced Drug Delivery Reviews*, 48:27-42 (2001) (XP009065056).

Zhang et al., "Induction of apoptosis in EMT-6 breast cancer cell in line by a Sigma-2 selective ligand," Am. Assoc. Cancer Research, Abstract 5353, 2005, 2 pages.

Zhang et al , "Inhibition of both autocrine and paracrine growth and propagation of human myeloid leukemia with antibodies directed against VEGF receptor 2," Proceedings of the American Association for Cancer Research, 44, 1479, (Abstract 6454), 2003, 2 pages.

Zhang et al., "Overexpression of Platelet-Derived Growth Factor Receptor α in Endothelial Cells of Hepatocellular Carcinoma Associated with High Metastatic Potential," *Clin. Cancer Res.*, 11(24):8557-8563 (2005).

Zhou et al., "Correlation Research on VEGF Testing in Primary Gastric Cancer and Clinical Pathology Factor," *Journal of Practical Oncology*, 20(2):103-105 (Apr. 25, 2006) with English translation.

Zhu et al., "Fibroblast growth factor receptor 3 inhibition by short hairpin RNAs leads to apoptosis in multiple myeloma," *Mol. Cancer Ther.*, 4(5):787-798 (2005).

Zhu et al., "Inhibition of human leukemia in an animal model with human antibodies directed against vascular endothelial growth factor receptor 2. Correlation between antibody affinity and biological activity," *Leukemia*, 17:604-611 (2003).

Zieger et al., "Role of activating fibroblast growth factor receptor 3 mutations in the development of bladder tumors," *Clin. Cancer Res.*, 11:7709-7719 (2005).

Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.

Zimmermann, "Electrical Breakdown, Electropermeabilization and Electrofusion", Rev. Physiol. Biochem. Pharmacol. 105:176-260 (1986).

Almarsson et al., "High-Throughput Surveys of Crystal Form Diversity of Highly Polymorphic Pharmaceutical Compounds," Crystal Growth & Design, Sep. 10, 2003, 3(6):927-933.

Amendment filed in KR App. Ser. No. 10-2009-7017694, dated Feb. 28, 2014, 7 pages.

Appeal for Reversal in CO App. Ser. No. 12-022608, dated Jan. 28, 2014, 17 pages (with English translation).

Argument filed in KR App. Ser. No. 10-2009-7017694, dated Feb. 28, 2014, 48 pages.

Gould, "Salt Selection for Basic Drugs," International Journal of Pharmaceutics, 33:201-217, (1986) (XP025813036).

Notice of Allowance in U.S. Appl. No. 12/524,754, dated Feb. 13, 2014, 18 pages.

Notice of Allowance in U.S. Appl. No. 12/741,682, dated Feb. 7, 2014, 11 pages.

Notice of Allowance in U.S. Appl. No. 13/083,338, dated Feb. 6, 2014, 15 pages.

Notice of Allowance in U.S. Appl. No. 13/205,328, dated Jan. 30, 2014, 11 pages.

Office Action in CA App. Ser. No. 2676796, dated Dec. 30, 2013, 5 pages.

Office Action in CN App. Ser. No. 200680020317.5, dated Mar. 4, 2014, 13 pages.

Office Action in EP App. Ser. No. 04807580.8, dated Mar. 18, 2014, 12 pages.

Office Action in EP App. Ser. No. 08704376.6, dated Feb. 24, 2014, 4 pages.

O'Reilly et al., "Hydrolysis of tert-Butyl Methyl Ether (MTBE) in Dilute Aqueous Acid," Environ. Sci. Technol., 2001, 35:3954-3961.

Patel et al., "The effect of excipients on the stability of levothyroxine sodium pentahydrate tablets," Int'l J Pharm., 2003, 264:35-43.

Response to Office Action in CN App. Ser. No. 200680020317.5 filed on Jan. 9, 2014, 7 pages (with English translation).

Response to Office Action in CN App. Ser. No. 201180030568.2 filed on Jan. 13, 2014, 46 pages (with English translation).

Response to Office Action in MX App. Ser. No. MX/a/2010/008187, dated Feb. 17, 2014, 7 pages (with English translation).

Response to Office Action in MX App. Ser. No. MX/a/2012/002011 filed on Jan. 16, 2014, 20 pages (with English translation).

Response to the Office Action issued for in App. Ser. No. 6415/CHENP/2008 filed on Jan. 17, 2014, 16 pages.

Stahl and Wermuth, "Handbook of Pharmaceutical Salts: Properties, selection, and use," 2002, pp. 117-122.

Submission documents re RCE filed in U.S. Appl. No. 12/741,682, dated Jan. 17, 2014, 1 page.

Submission documents re RCE in U.S. Appl. No. 12/439,339, dated Jan. 27, 2014, 1 page.

Office Action in U.S. Appl. No. 11/997,543, dated Mar. 11, 2014, 20 pages.

Search Report in EP App. Ser. No. 11798224.9, dated Mar. 21, 2014, 1 page.

Office Action in KR App. Ser. No. 10-2009-7017694, dated Jan. 29, 2014, 26 pages (with English translation).

Response filed in PH App. Ser. No. 1-2011-502441, dated Feb. 28, 2014, 4 pages.

Office Action in PH App. Ser. No. 1-2011-502441, dated Feb. 19, 2014, 2 pages.

Office Action in U.S. Appl. No. 11/662,425, dated Feb. 27, 2014, 152 pages.

Search Report in EP App. Ser. No. 11798224.9, dated Mar. 4, 2014, 6 pages.

Office Action in U.S. Appl. No. 12/039,381, dated Jan. 9, 2014, 16 pages.

Submission documents re RCE in U.S. Appl. No. 12/524,754 filed on Feb. 3, 2014, 1 page.

Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.

Written Submission regarding hearing in IN App. Ser. No. 1571/CHENP/2007 filed on Jan. 23, 2014, 8 pages.

Zhang et al., "Synergic antiproliferative effect of DNA methyltransferase inhibitor in combination with anticancer drugs in gastric carcinoma," Cancer Sci., Sep. 2006, 97(9):938-944.

* cited by examiner

THERAPEUTIC AGENT FOR TUMOR

TECHNICAL FIELD

The present invention relates to a therapeutic agent for tumor for combined use of a compound having a kinase inhibitory effect and a compound having a BRAF inhibitory effect. Particularly, the present invention relates to a therapeutic agent for tumor for combined use of a compound having a multi-tyrosine kinase inhibitory effect and N-(3-{[5-(4-chlorophenyl)-1H-pyrrolo[2,3-b]pyridin-3-yl]carbonyl}-2,4-difluorophenyl)propane-1-sulfonamide (PLX4032).

BACKGROUND ART

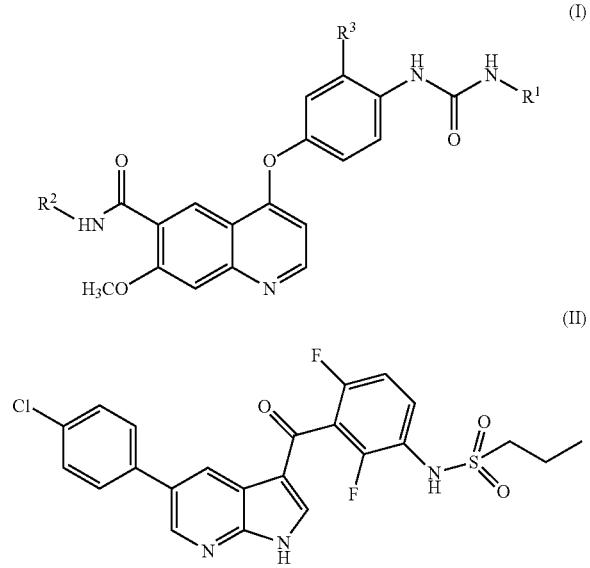

wherein $R^1$ is $C_{1-6}$ alkyl or $C_{3-8}$ cycloalkyl, $R^2$ is a hydrogen atom or $C_{1-6}$ alkoxy, and $R^3$ is a hydrogen atom or a halogen atom.

The compound represented by Formula (I) has anti-angiogenic actions (Patent Literature 1), inhibitory effects (Patent Literatures 2 to 5) against tyrosine kinases which are reported to be involved in malignant alteration of tumors (Non-Patent Literatures 1 to 5), and the like; and is known as a therapeutic agent for various tumors such as thyroid cancer, lung cancer, melanoma, endometrial cancer, gastric cancer, bladder cancer, renal cancer, glioma, liver cancer, and ovarian cancer.

Meanwhile, N-(3-{[5-(4-chlorophenyl)-1H-pyrrolo[2,3-b]pyridin-3-yl]carbonyl}-2,4-difluorophenyl)propane-1-sulfonamide is a compound represented by the formula (II), which is known as a potent BRAF kinase activity inhibitor (Patent Literature 6). This compound is referred to as PLX4032, which is currently under development as a therapeutic agent for tumor such as melanoma.

In general, therapeutic agents for tumor are often not effective for all of the patients when they were used individually. Thus, attempts have been made so far to increase the cure rate by combination of plural antitumor agents (Patent Literatures 7 to 9).

CITATION LIST

Patent Literature

Patent Literature 1: US Patent Application Publication No. 2004-053908
Patent Literature 2: US Patent Application Publication No. 2004-253205
Patent Literature 3: US Patent Application Publication No. 2010-105031
Patent Literature 4: US Patent Application Publication No. 2009-209580
Patent Literature 5: US Patent Application Publication No. 2009-264464
Patent Literature 6: WO 2007/002325
Patent Literature 7: WO 2009/140549
Patent Literature 8: US Patent Application Publication No. 2004-259834
Patent Literature 9: U.S. Pat. No. 6,217,866

Non Patent Literature

Non Patent Literature 1: Lasota et al., "Mutations in Exons 9 and 13 of KIT Gene Are Rare Events in Gastrointestinal Stromal Tumors", American Journal of Pathology, vol. 157, p. 1091-1095, 2000.
Non Patent Literature 2: Berdel et al., "Recombinant Human Stem Cell Factor Stimulates Growth of a Human Glioblastoma Cell Line Expressing c-kit Protooncogenl", Cancer Research, vol. 52, p. 3498-3502, 1992.
Non Patent Literature 3: Lennartsson et al., "The stem cell factor receptor/c-Kit as a drug target in cancer", Current Cancer Drug Targets, vol. 6, p. 65-75, 2006.
Non Patent Literature 4: Turner et al., "Fibroblast growth factor signaling: from development to cancer", Nature Reviews Cancer, vol. 10, p. 116-129, 2010.
Non Patent Literature 5: Wells et al, "Targeting the RET Pathway in Thyroid Cancer", Clinical Cancer Research, vol. 15, p. 7119-7123, 2009.

SUMMARY OF INVENTION

Technical Problem

However, the therapeutic effects, which have been reported so far, obtained by combination of plural therapeutic agents for tumor were insufficient, and hence development of a novel combination therapy using therapeutic agents for tumor has been expected.

Solution to Problem

In view of such circumstances, the present inventors intensively studied to discover that administration of a combination of the compound represented by Formula (I) and the compound having a kinase inhibitory effect to a patient suffering from a tumor attains an unexpectedly excellent antitumor effect, thereby completing the present invention.

That is, the present invention provides [1] to [8] below.

[1] A therapeutic agent for tumor for combined use of:
a compound or pharmaceutically acceptable salt thereof represented by Formula (I):

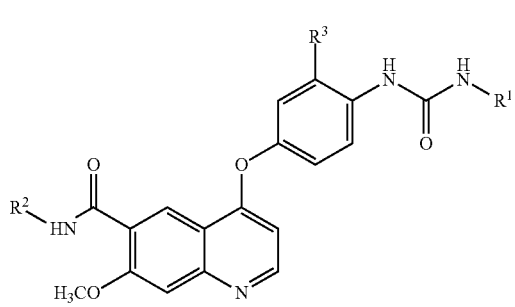

(I)

wherein R¹ is $C_{1-6}$ alkyl or $C_{3-8}$ cycloalkyl,
R² is a hydrogen atom or $C_{1-6}$ alkoxy, and
R³ is a hydrogen atom or a halogen atom; and
a compound represented by Formula (II):

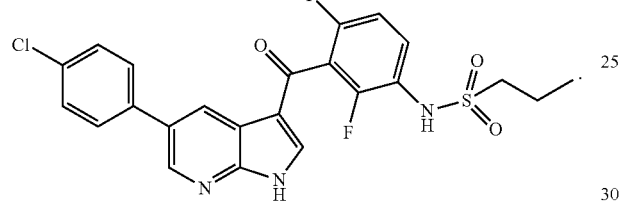

(II)

[2] A therapeutic agent for tumor for simultaneous or separate administration of a compound or pharmaceutically acceptable salt thereof represented by the above Formula (I), and a compound represented by the above Formula (II).

[3] A therapeutic agent for tumor comprising a compound or pharmaceutically acceptable salt thereof represented by the above Formula (I), and a compound represented by the above Formula (II).

[4] A compound represented by the above Formula (II) for therapy of a tumor by combined use with a compound or pharmaceutically acceptable salt thereof represented by the above Formula (I).

[5] A compound or pharmaceutically acceptable salt thereof represented by the above Formula (I) for therapy of a tumor by combined use with a compound represented by the above Formula (II).

[6] A method of treating a tumor, wherein a compound or pharmaceutically acceptable salt thereof represented by the above Formula (I), and a compound represented by the above Formula (II) are used in combination.

[7] A pharmaceutical composition comprising a compound or pharmaceutically acceptable salt thereof represented by the above Formula (I), a compound represented by the above Formula (II), and a vehicle.

[8] A kit comprising: a pharmaceutical composition comprising a compound or pharmaceutically acceptable salt thereof represented by the above Formula (I) and a vehicle; and a pharmaceutical composition comprising a compound represented by the above Formula (II), and a vehicle.

The compound represented by the above Formula (I) is preferably one or more compounds selected from the group consisting of 4-[3-chloro-4-(cyclopropylaminocarbonyl)aminophenoxy]-7-methoxy-6-quinolinecarboxamide:

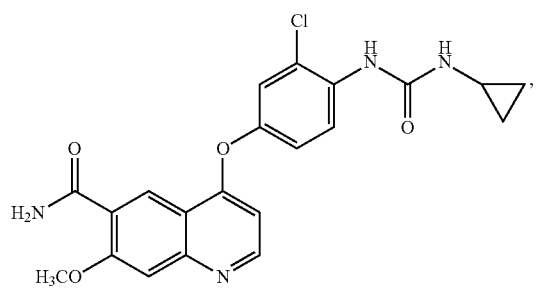 [SMILES: COc1cc2nccc(Oc3ccc(NC(=O)NC4CC4)c(Cl)c3)c2cc1C(N)=O]

4-[3-chloro-4-(methylaminocarbonyl)aminophenoxy]-7-methoxy-6-quinolinecarboxamide:

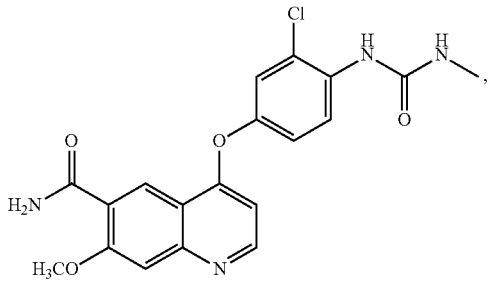 [SMILES: CNC(=O)Nc1ccc(Oc2ccnc3cc(OC)c(C(N)=O)cc23)cc1Cl]

4-[3-chloro-4-(ethylaminocarbonyl)aminophenoxy]-7-methoxy-6-quinolinecarboxamide:

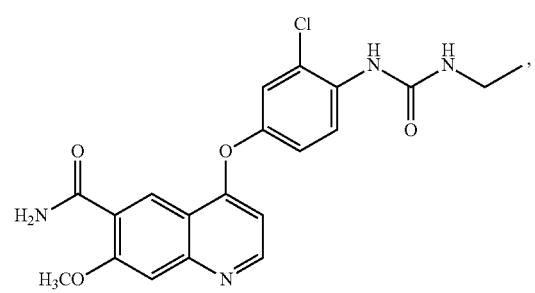 [SMILES: CCNC(=O)Nc1ccc(Oc2ccnc3cc(OC)c(C(N)=O)cc23)cc1Cl]

N6-methoxy-4-(3-chloro-4-{[(cyclopropylamino)carbonyl)amino]phenoxy}-7-methoxy-6-quinolinecarboxamide:

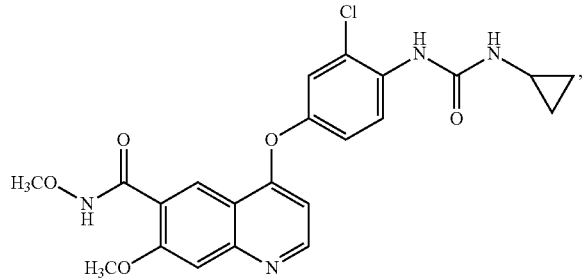 [SMILES: CONC(=O)c1cc2c(Oc3ccc(NC(=O)NC4CC4)c(Cl)c3)ccnc2cc1OC]

and
N6-methoxy-4-(3-chloro-4-{[(ethylamino)carbonyl]amino}phenoxy)-7-methoxy-6-quinolinecarboxamide:

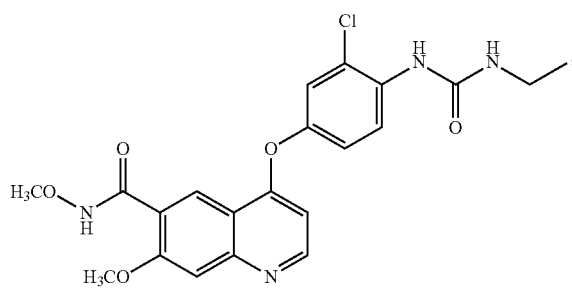

and more preferably
4-[3-chloro-4-(cyclopropylaminocarbonyl)aminophenoxy]-7-methoxy-6-quinolinecarboxamide:

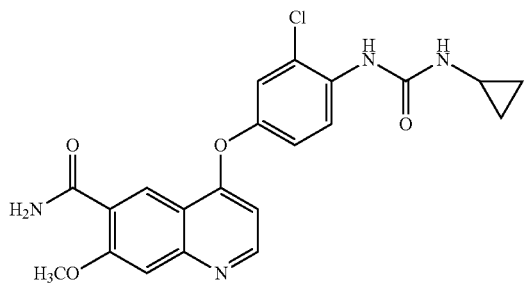 [SMILES: COc1cc2nccc(Oc3ccc(NC(=O)NC4CC4)c(Cl)c3)c2cc1C(N)=O]

(hereinafter, also sometimes expressed as Compound A).

Advantageous Effects of Invention

The present invention provides a therapeutic agent for tumor for combined use of a compound having a multi-tyrosine kinase inhibitory effect and a compound having a BRAF kinase activity inhibitory effect. Such a therapeutic agent for tumor exhibits an excellent antitumor effect compared to cases where these are individually used, and exhibits antitumor effects against various cancer types.

DESCRIPTION OF EMBODIMENTS

Figure 1:
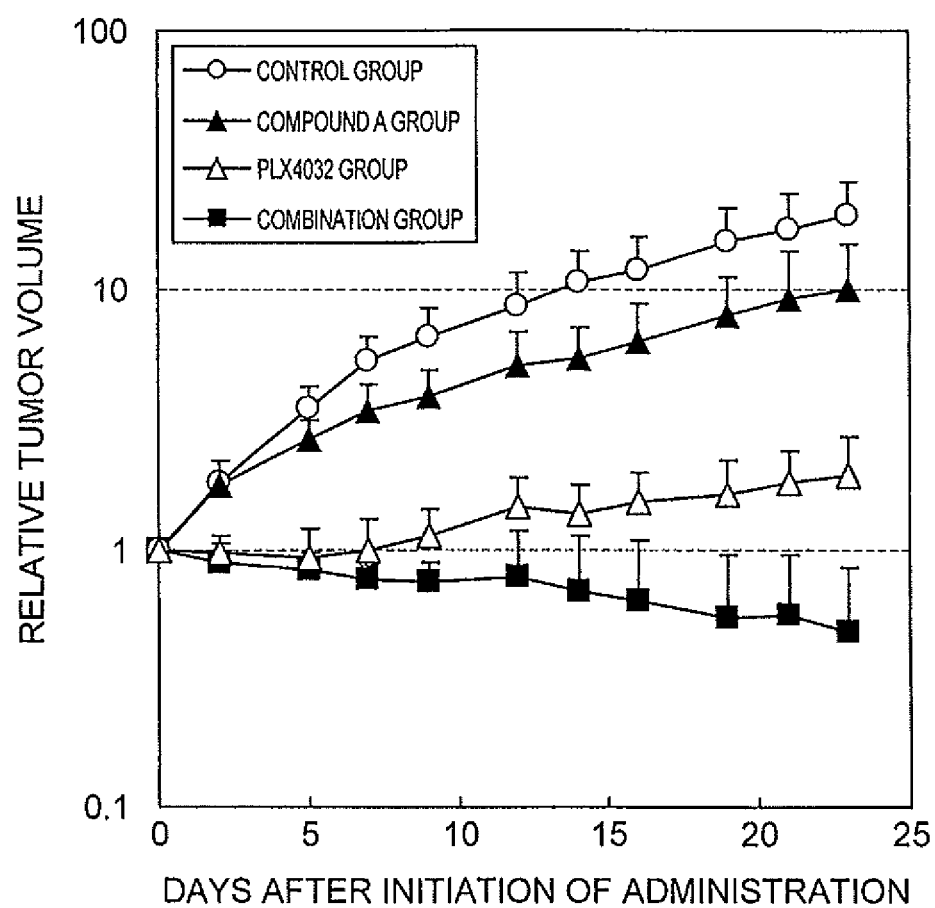
FIG. 1 is a graph showing a combined effect of Compound A and PLX4032 in a model animal to which human melanoma cell line (A375) was transplanted.

The compound or pharmaceutically acceptable salt thereof represented by Formula (I) according to the present invention can be produced by the method described in Patent Literature 1. Further, the compound represented by Formula (II) (hereinafter, also simply referred to as PLX4032) according to the present invention can be produced by the method described in Patent Literature 6.

Also, a compound known to have a BRAF inhibitory effect can be used as the therapeutic agent for tumor according to the present invention in place of PLX4032. Examples of such a compound include 4-{4-[({[4-chloro-3-(trifluoromethyl)phenyl]amino}carbonyl)amino]phenoxy}-N-methylpyridine-2-carboxamide 4-methylbenzenesulfonate (sorafenib)

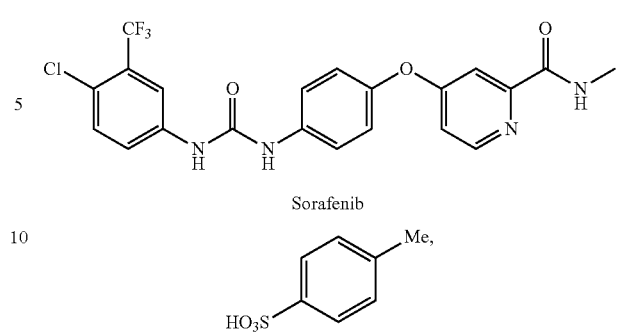

Sorafenib 1-methyl-5-({2-[4-(trifluoromethyl)-1H-imidazol-2-yl}pyridin-4-yl]oxy)-N-[4-(trifluoromethyl)phenyl]-1H-benzimidazol-2-amine (RAF-265)

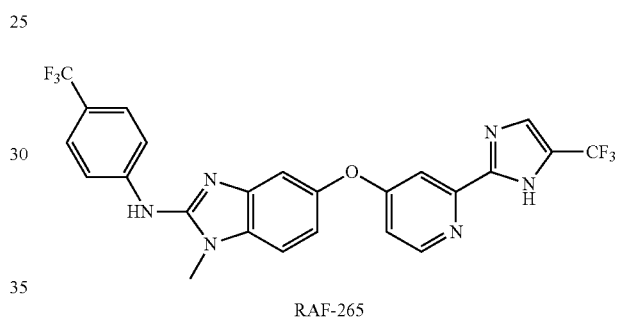

RAF-265

5-(2-{4-[2-(dimethylamino)ethoxy]phenyl}-4-pyridin-4-yl-1H-imidazol-5-yl)indan-1-one oxime (SB-590885)

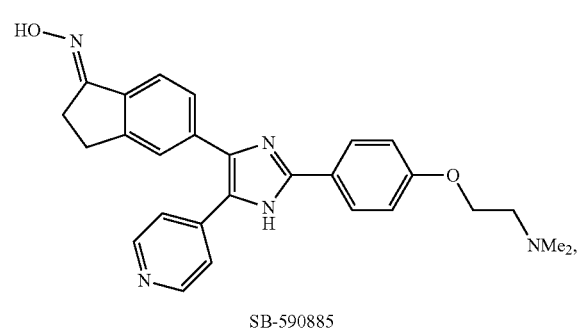 [SMILES: CN(C)CCOc1ccc(-c2nc(-c3ccc4c(c3)CC/C4=N\O)c(-c3ccncc3)[nH]2)cc1]

SB-590885

1-N-(4-chlorophenyl)-6-methyl-5-N-[3-(9H-purin-6-yl)pyridin-2-yl]isoquinoline-1,5-diamine (hereinbelow, abbreviated as aminoisoquinoline)

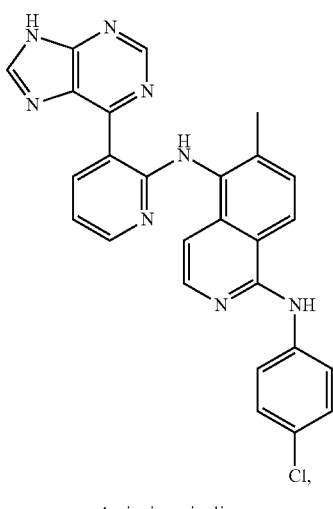

Aminoisoquinoline and [3-(3-hydroxy-5-methylphenyl)-4-(2-{[(2S)-2-hydroxypropyl]amino}pyrimidin-4-yl)-1H-pyrazol-1-yl]acetonitrile (PF-0419789)

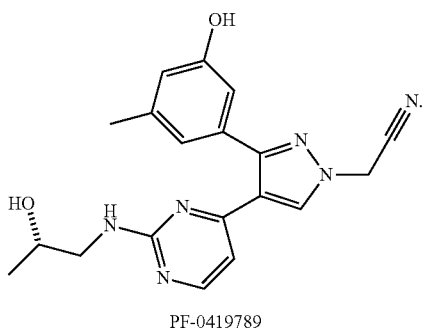 [SMILES: Cc1cc(O)cc(-c2nn(CC#N)cc2-c2ccnc(NC[C@H](C)O)n2)c1]

PF-0419789

Sorafenib, RAF-265, SB-590885, aminoisoquinoline, and PF-0419789 can each be produced by the methods described in WO2000/041698, U.S. Patent Application Publication No. 2007-0049622, WO 2002/024680, WO 2008/153947, and WO 2007/105058, respectively.

Examples of the pharmaceutically acceptable salt include salts with inorganic acids, salts with organic acids, salts with inorganic bases, salts with organic bases, and salts with acidic or basic amino acids.

Preferred examples of the salts with inorganic acids include salts with hydrochloric acid, hydrobromic acid, sulfuric acid, nitric acid, phosphoric acid and the like. Preferred examples of the salts with organic acids include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid and the like.

Preferred examples of the salts with inorganic bases include alkaline metal salts such as a sodium salt and a potassium salt; alkaline earth metal salts such as a calcium salt and a magnesium salt; an aluminum salt; and an ammonium salt. Preferred examples of the salts with organic bases include salts with diethylamine, diethanolamine, meglumine, N,N-dibenzylethylenediamine and the like.

Preferred examples of the salts with acidic amino acids include salts with aspartic acid, glutamic acid and the like.

Preferred examples of the salts with basic amino acids include salts with arginine, lysine, ornithine and the like.

Especially preferred pharmaceutically acceptable salts are salts with organic acids.

The therapeutic agent for tumor of the present invention may be orally administered in the form of a solid formulation such as a tablet, granule, fine granule, powder or capsule, or in the form of a liquid, jelly, syrup or the like.

Further, the therapeutic agent for tumor of the present invention may be parenterally administered in the form of an injection, suppository, ointment, cataplasm or the like.

The dose of the compound or pharmaceutically acceptable salt thereof represented by Formula (I) may be appropriately selected depending on the degrees of symptoms, age, sex and body weight of the patient, difference in sensitivity, route, time and interval of administration, type of pharmaceutical formulation, and/or the like. Usually, in cases where oral administration is carried out for an adult (60 kg body weight), the dose is 1 to 600 mg, preferably 5 to 400 mg per day, more preferably 5 to 200 mg. This may be administered at one time, or dividedly at 2 or 3 times per day.

The dose of PLX4032 may be appropriately selected as in the case described above. Usually, in cases where oral administration is carried out for an adult (60 kg body weight), the dose is 1 to 2000 mg, preferably 100 to 1500 mg, more preferably 240 to 1200 mg per day. This may be administered at one time, or dividedly at 2 or 3 times per day.

In cases where an oral solid formulation is prepared, a vehicle, and, as required, a binder, disintegrant, lubricant, coloring agent, flavoring agent and/or the like may be added to the principal component, that is, a compound or pharmaceutically acceptable salt thereof represented by Formula (I), and PLX4032, to prepare, thereafter, a tablet, granule, fine granule, powder, capsule or the like according to a conventional method.

Examples of the vehicle include lactose, corn starch, white soft sugar, glucose, sorbitol, crystalline cellulose and silicon dioxide. Examples of the binder include polyvinyl alcohol, ethylcellulose, methylcellulose, gum Arabic, hydroxypropylcellulose and hydroxypropylmethylcellulose. Examples of the lubricant include magnesium stearate, talc and silica. Examples of the coloring agent include titanium oxide, iron sesquioxide, yellow iron sesquioxide, cochineal, carmine and riboflavin. Examples of the flavoring agent include cocoa powder, ascorbic acid, tartaric acid, peppermint oil, borneol and cinnamon powder. These tablets and granules may be coated as required.

In cases where an injection is prepared, a pH adjustor, buffering agent, suspending agent, solubilizer, stabilizer, isotonic agent, preservative and/or the like may be added as required to the principal component, to prepare an intravenous, subcutaneous or intramuscular injection, or an intravenous drip infusion. As required, these may be prepared into lyophilized products by conventional methods.

Examples of the suspending agent include methylcellulose, polysorbate 80, hydroxyethylcellulose, gum Arabic, powdered tragacanth, sodium carboxymethylcellulose and polyoxyethylene sorbitan monolaurate.

Examples of the solubilizer include polyoxyethylene hydrogenated castor oil, polysorbate 80, nicotinamide, polyoxyethylene sorbitan monolaurate, macrogol and glycerin fatty acid ester.

Examples of the stabilizer include sodium sulfite and sodium metabisulfite. Examples of the preservative include methyl parahydroxybenzoate, ethyl parahydroxybenzoate, sorbic acid, phenol, cresol and chlorocresol.

The therapeutic agent for tumor of the present invention may be prepared by formulating a compound or pharmaceutically acceptable salt thereof represented by Formula (I), and PLX4032 separately, and the both may be administered either at the same time or separately. Further, the two formulations may be placed in a single package, to provide the so called kit formulation. Further, the both compounds may be contained in a single formulation.

The type of the tumor to be treated with the therapeutic agent for tumor according to the present invention is not restricted, and examples thereof include cancers such as fibroma, adipoma, myxoma, chondroma, osteoma, angioma, hemangioendothelioma, lymphoma, myeloma, myeloid sarcoma, reticuloma, reticulosarcoma, melanoma, myoma, neuroma, glioma, neurinoma, sarcoma, osteosarcoma, myoma, fibrosarcoma, papilloma, adenoma, cystoma, brain tumor, cervical cancer, tongue cancer, pharyngeal cancer, laryngeal cancer, thyroid cancer, esophagus cancer, lung cancer, breast cancer, pancreatic cancer, gastric cancer, small intestinal cancer in duodenum, jejunum, ileum and the like, large bowel cancer in colon, caecum, rectum and the like, bladder cancer, renal cancer, liver cancer, gallbladder cancer, prostate cancer, uterine cancer, uterine cervical cancer, and ovarian cancer, mixed tumors thereof, and a metastatic tumor.

Industrial Applicability

EXAMPLES

The present invention is described in more detail by way of Examples below. Example 1 Tumor Proliferation Inhibitory Effect of the Combined Use of Compound A and PLX4032 on a Human Melanoma Cell Line (A375)

Using five nude mice in one group (CAnN.Cg-Foxn1nu/CrlCrlj, female, Charles River Laboratories Japan, Inc.), the antitumor effect of administration of Compound A, PLX4032, or both of these compounds was evaluated. The human-derived melanoma cell line A375 (ATCC) was suspended in PBS (Wako Pure Chemical Industries, Ltd) at a density of $5 \times 10^6$ cells/ml, followed by thorough mixing. The resulting mixture was subcutaneously transplanted at the right flank of the body of each mouse in an amount of 0.1 mL. Fourteen days after transplantation, the major axis and the minor axis of a tumor were measured by a digital caliper (Digimatic™ caliper, Mitsutoyo Corporation). The mice were grouped so that the average value of tumor volume was nearly equal among the groups. Also, the tumor volume was calculated according to the equations below.

Tumor volume (mm³)=major axis (mm)×minor axis (mm)×minor axis (mm)/2

Compound A was dissolved in purified water at a concentration of 1 mg/mL. Also, PLX4032 was dissolved in DMSO at a concentration of 200 mg/ml. Further, the resulting solution was diluted 20-fold with a 1% aqueous solution of methylcellulose to prepare a 10 mg/mL PLX4032 suspension.

A control group, a Compound A group, a PLX4032 group, and a Compound A and PLX4032-combination group (hereinbelow, expressed as a combination group) were set up. The aqueous solution of Compound A or the PLX4032 suspension was orally administered to the mice in the Compound A group or the PLX4032 group, respectively, once daily at 10 mL/kg. To the combination group mice, the above drug solutions were each orally administered once daily at 10 mL/kg. The administration period was 23 days. Also, administration was not given to the control group mice.

Figure 2:
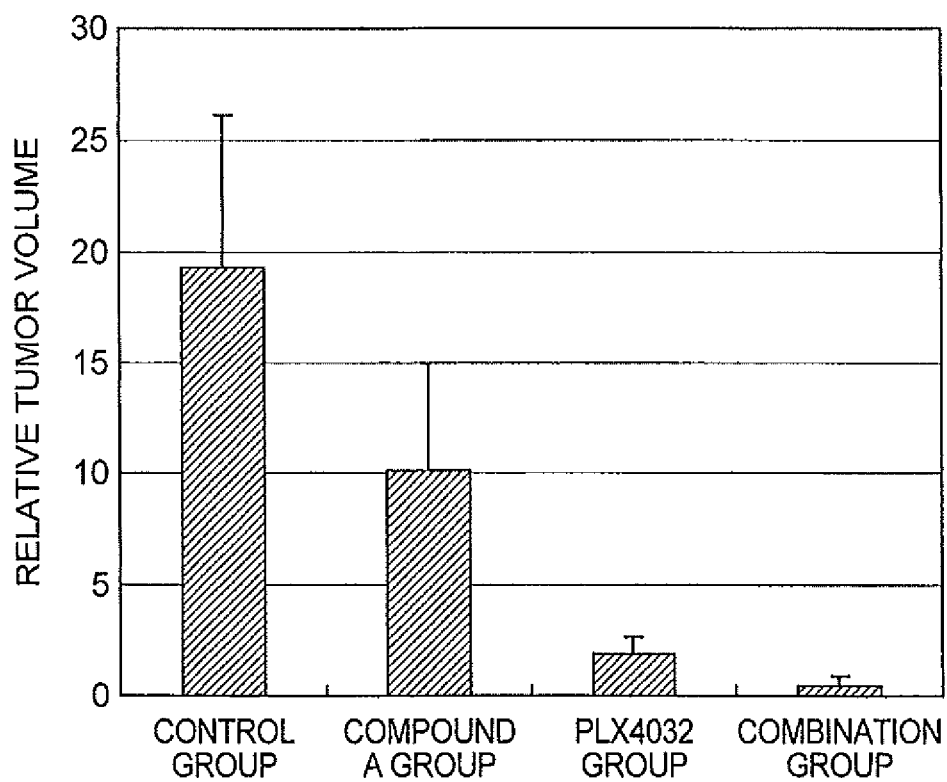
FIG. 2 is a graph showing the relative tumor volume of each group on the 23$^{rd}$ day after initiation of administration.

The tumor volume was measured on the initial day of administration and on the $2^{nd}$, $5^{th}$, $7^{th}$, $9^{th}$, $12^{th}$, $14^{th}$, $16^{th}$, $19^{th}$, $21^{st}$, and $23^{rd}$ days after initiation of administration. The ratio of the tumor volume on each day of measurement relative to the tumor volume on the initial day of administration was calculated as a relative tumor volume (hereinbelow, expressed as RTV). Further, the average value of RTV of mice in each group was calculated. The changes in the average value of RTV with time were shown in Table 1 and FIG. 1 and the value of each group on Day 23 was shown in FIG. 2.

TABLE 1

| | Day 2 | Day 5 | Day 7 | Day 9 | Day 12 |
|---|---|---|---|---|---|
| Control group | 1.80 | 3.47 | 5.29 | 6.52 | 8.77 |
| Compound A group | 1.77 | 2.62 | 3.40 | 3.85 | 5.12 |
| PLX4032 group | 0.98 | 0.94 | 1.00 | 1.13 | 1.46 |
| Combination group | 0.90 | 0.84 | 0.77 | 0.75 | 0.78 |

| | Day 14 | Day 16 | Day 19 | Day 21 | Day 23 |
|---|---|---|---|---|---|
| Control group | 10.66 | 11.95 | 15.49 | 17.29 | 19.31 |
| Compound A group | 5.40 | 6.30 | 7.89 | 9.16 | 10.17 |
| PLX4032 group | 1.38 | 1.52 | 1.63 | 1.80 | 1.93 |
| Combination group | 0.69 | 0.63 | 0.55 | 0.56 | 0.48 |

The invention claimed is:

1. A method of treating a tumor, comprising administering to a patient in need thereof a combination of:
   a compound represented by Formula (I) or a pharmaceutically acceptable salt thereof:

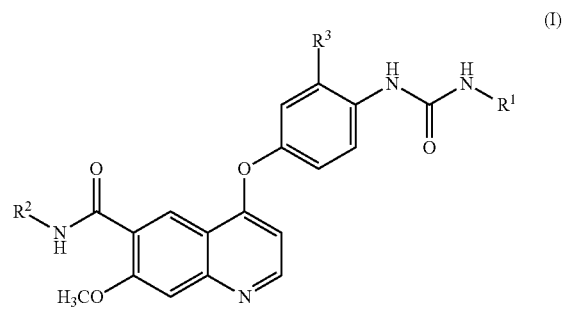

(I)

wherein $R^1$ is $C_{1-6}$ alkyl or $C_{3-8}$ cycloalkyl,
$R^2$ is a hydrogen atom or $C_{1-6}$ alkoxy, and
$R^3$ is a hydrogen atom or a halogen atom; and
a compound represented by Formula (II):

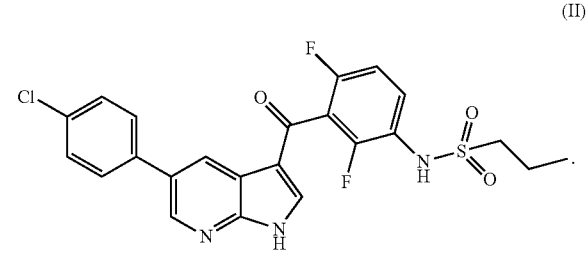 [SMILES: CCCS(=O)(=O)Nc1ccc(F)c(C(=O)c2c[nH]c3ncc(-c4ccc(Cl)cc4)cc23)c1F]

(II)

2. A pharmaceutical composition comprising:
a compound represented by Formula (I) or a pharmaceutically acceptable salt thereof:

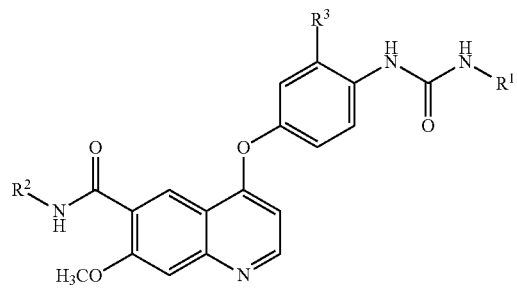

(I)

wherein $R^1$ is $C_{1-6}$ alkyl or $C_{3-8}$ cycloalkyl,
$R^2$ is a hydrogen atom or $C_{1-6}$ alkoxy, and
$R^3$ is a hydrogen atom or a halogen atom; and
a compound represented by Formula (II):

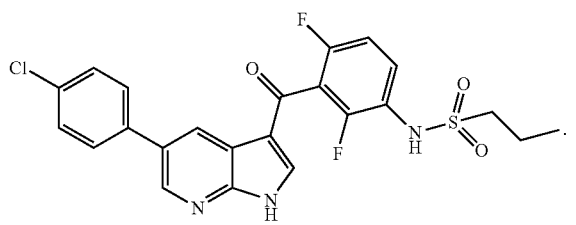

(II)

3. The method of claim 1, wherein the compound represented by Formula (I) is selected from the group consisting of:
4-[3-chloro-4-(cyclopropylaminocarbonyl)aminophenoxy]-7-methoxy-6-quinolinecarboxamide:

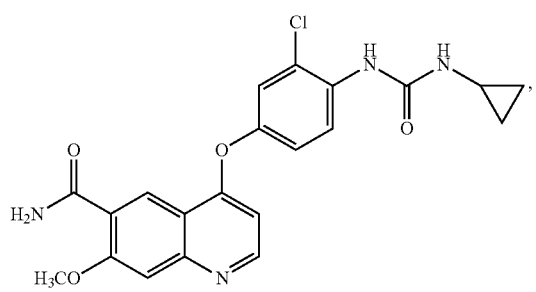 [SMILES: COc1cc2nccc(Oc3ccc(NC(=O)NC4CC4)c(Cl)c3)c2cc1C(N)=O]

4-[3-chloro-4-(methylaminocarbonyl)aminophenoxy]-7-methoxy-6-quinolinecarboxamide:

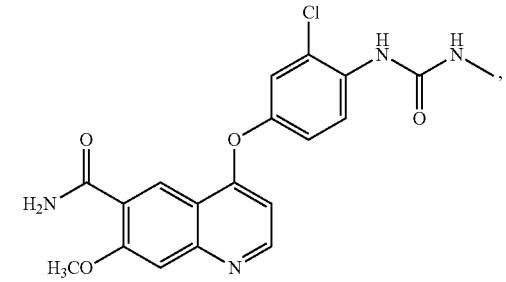 [SMILES: CNC(=O)Nc1ccc(Oc2ccnc3cc(OC)c(C(N)=O)cc23)cc1Cl]

4-[3-chloro-4-(ethylaminocarbonyl)aminophenoxy]-7-methoxy-6-quinolinecarboxamide:

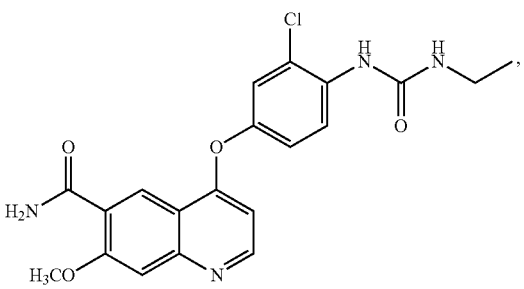 [SMILES: CCNC(=O)Nc1ccc(Oc2ccnc3cc(OC)c(C(N)=O)cc23)cc1Cl]

N6-methoxy-4-(3-chloro-4-{[(cyclopropylamino)carbonyl)amino]phenoxy}-7-methoxy-6-quinolinecarboxamide:

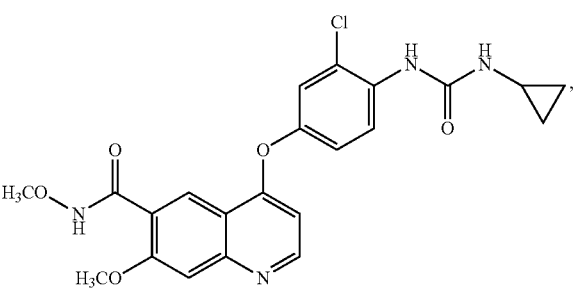 [SMILES: CONC(=O)c1cc2c(Oc3ccc(NC(=O)NC4CC4)c(Cl)c3)ccnc2cc1OC]

and
N6-methoxy-4-(3-chloro-4-{[(ethylamino)carbonyl]amino}phenoxy)-7-methoxy-6-quinolinecarboxamide:

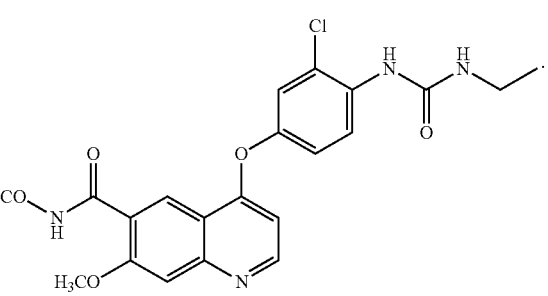

4. The method of claim 1, wherein the compound represented by Formula (I) is 4-[3-chloro-4-(clopropylaminocarbonyl)aminophenoxy]-7-methoxy-6-quinolinecarboxamide:

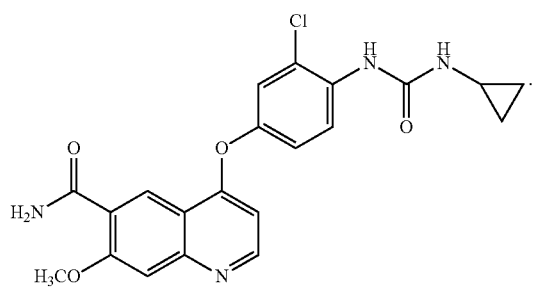 [SMILES: COc1cc2nccc(Oc3ccc(NC(=O)NC4CC4)c(Cl)c3)c2cc1C(N)=O]

5. The method of claim 1, comprising simultaneous administration of the compound represented by Formula (I), or a pharmaceutically acceptable salt thereof, and the compound represented by Formula (II).

6. The method of claim 1, comprising separate administration of the compound represented by Formula (I), or a pharmaceutically acceptable salt thereof, and the compound represented by Formula (II).

7. The method of claim 1, wherein the tumor is thyroid cancer, lung cancer, melanoma, endometrial cancer, gastric cancer, bladder cancer, renal cancer, glioma, liver cancer, or ovarian cancer.

8. The method of claim 1, wherein the tumor is melanoma.

9. The pharmaceutical composition of claim 2, wherein the compound represented by Formula (I) is selected from the group consisting of:

4- [3-chloro-4-(cyclopropylaminocarbonyl)aminophenoxy]-7-methoxy -6-quinolinecarboxamide:

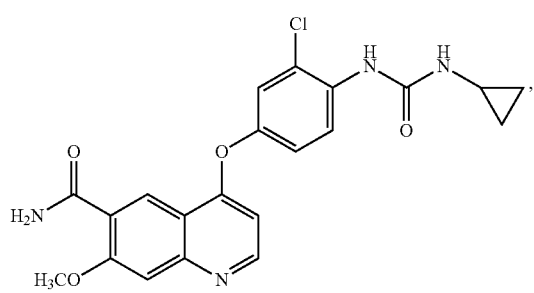 [SMILES: COc1cc2nccc(Oc3ccc(NC(=O)NC4CC4)c(Cl)c3)c2cc1C(N)=O]

4-[3-chloro-4-(methylaminocarbonyl)aminophenoxy]-7-methoxy-6-quinolinecarboxamide:

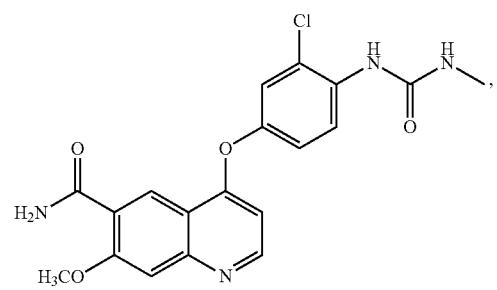

4-[3-chloro-4-(ethylaminocarbonyl)aminophenoxy]-7-methoxy-6-quinolinecarboxamide:

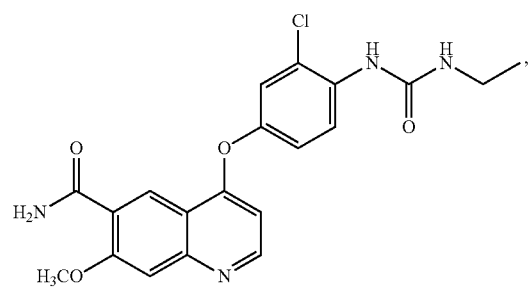 [SMILES: CCNC(=O)Nc1ccc(Oc2ccnc3cc(OC)c(C(N)=O)cc23)cc1Cl]

N6-methoxy-4-(3-chloro-4-{[(cyclopropylamino)carbonyl]amino]phenoxy}-7-methoxy-6-quinolinecarboxamide:

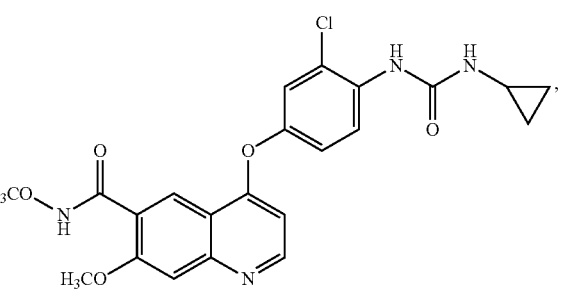

and
N6-methoxy-4-(3-chloro-4-{[(ethylamino)carbonyl]amino}phenoxy)-7-methoxy-6-quinolinecarboxamide:

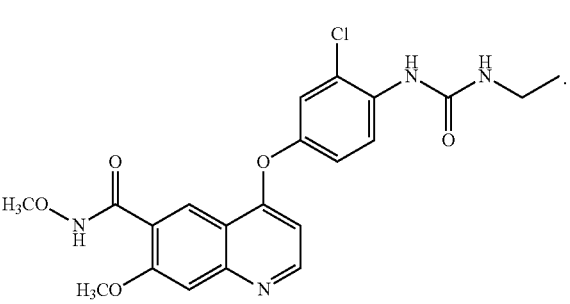 [SMILES: CCNC(=O)Nc1ccc(Oc2ccnc3cc(OC)c(C(=O)NOC)cc23)cc1Cl]

10. The pharmaceutical composition of claim 2, wherein the compound represented by Formula (I) is 4 -[3-chloro-4-(cyclopropylaminocarbonyl)aminophenoxy]-7-methoxy-6-quinolinecarboxamide:

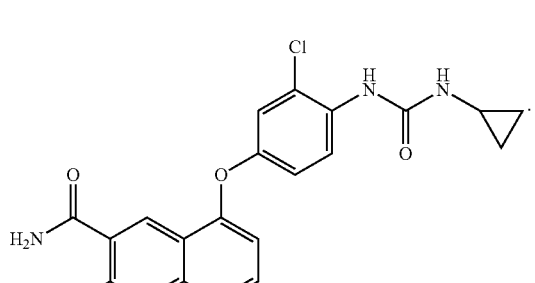

* * * * *